United States Patent
Dodda et al.

(10) Patent No.: US 9,586,913 B2
(45) Date of Patent: Mar. 7, 2017

(54) PROCESSES FOR THE PREPARATION OF LINEZOLID USING NOVEL INTERMEDIATES

(71) Applicant: Symed Labs Limited, Hyderabad (IN)

(72) Inventors: Mohan Rao Dodda, Hyderabad (IN); Venkat Reddy Buthukuri, Hyderabad (IN)

(73) Assignee: Symed Labs Limited (IN)

( * ) Notice: Subject to any disclaimer, the term of this patent is extended or adjusted under 35 U.S.C. 154(b) by 0 days.

(21) Appl. No.: 14/785,960

(22) PCT Filed: Apr. 25, 2013

(86) PCT No.: PCT/IN2013/000278
§ 371 (c)(1),
(2) Date: Oct. 21, 2015

(87) PCT Pub. No.: WO2014/174522
PCT Pub. Date: Oct. 30, 2014

(65) Prior Publication Data
US 2016/0102064 A1    Apr. 14, 2016

(51) Int. Cl.
*C07D 263/24*  (2006.01)
*C07D 263/20*  (2006.01)
*C07D 209/48*  (2006.01)
*C07D 295/135* (2006.01)

(52) U.S. Cl.
CPC ......... *C07D 263/24* (2013.01); *C07D 209/48* (2013.01); *C07D 263/20* (2013.01); *C07D 295/135* (2013.01)

(58) Field of Classification Search
None
See application file for complete search history.

(56) References Cited

U.S. PATENT DOCUMENTS

| | | |
|---|---|---|
| 7,291,614 B2 | 11/2007 | Fine et al. |
| 2006/0247435 A1 | 11/2006 | Mohan Rao et al. |
| 2009/0156806 A1 | 6/2009 | Colombo et al. |
| 2011/0034465 A1 | 2/2011 | Bodhuri et al. |
| 2011/0275805 A1 | 11/2011 | Wang et al. |

OTHER PUBLICATIONS

Reddy, Ganta Madhusudhan. A New Practical Synthesis of Linezolid: An Antibacterial Drug. Letters in Organic Chemistry. 2010, 7, 45-49.*
Park, HoonGyu. A New Method for the Oxazolidinone Key Intermediate of Linezolid and its Formal Synthesis. Bull. Korean Chem. Soc. 2012, 33(4), 1389-1392.*
Database Registry Chemical Abstracts Service, Columbus, Ohio, Accession No. RN 1158467-29-8, Entered STN: Jun. 16, 2009.*
International Search Report for PCT/IN2013/000278 dated Dec. 6, 2013.

* cited by examiner

*Primary Examiner* — Samantha Shterengarts
(74) *Attorney, Agent, or Firm* — Caesar Rivise, PC

(57) ABSTRACT

Provided herein are improved, commercially viable and industrially advantageous processes for the preparation of Linezolid, in high yield and purity, using novel intermediates. In one aspect, provided herein are efficient, industrially advantageous and environmentally friendly processes for the preparation of linezolid, in high yield and with high purity, using novel intermediates. The processes disclosed herein avoid the tedious and cumbersome procedures of the prior processes, thereby resolving the problems associated with the processes described in the prior art, which is more convenient to operate at lab scale and in commercial scale operations.

23 Claims, No Drawings

PROCESSES FOR THE PREPARATION OF LINEZOLID USING NOVEL INTERMEDIATES

FIELD OF THE INVENTION

The present invention relates to improved, commercially viable and industrially advantageous processes for the preparation of Linezolid, in high yield and purity, using novel intermediates.

BACKGROUND OF THE INVENTION

U.S. Pat. No. 5,688,792 (hereinafter referred to as the US'792 patent), assigned to Pharmacia & Upjohn Company, discloses a variety of oxazine and thiazine oxazolidinone derivatives and their stereochemically isomeric forms, processes for their preparation, pharmaceutical compositions comprising the derivatives, and method of use thereof. These compounds are useful antimicrobial agents, effective against a number of human and veterinary pathogens, particularly gram-positive aerobic bacteria such as multiply-resistant staphylococci, streptococci and enterococci as well as anaerobic organisms and acid-fast organisms. Among them, Linezolid, a member of the oxazolidinone class of drugs and chemically named as N-[[(5S)-3-[3-fluoro-4-(4-morpholinyl)phenyl]-2-oxo-5-oxazolidinyl]methyl]acetamide, is active against most Gram-positive bacteria that cause disease, including streptococci, vancomycin-resistant enterococci (VRE), and methicillin-resistant *Staphylococcus aureus* (MRSA). Linezolid is represented by the following structural formula I:

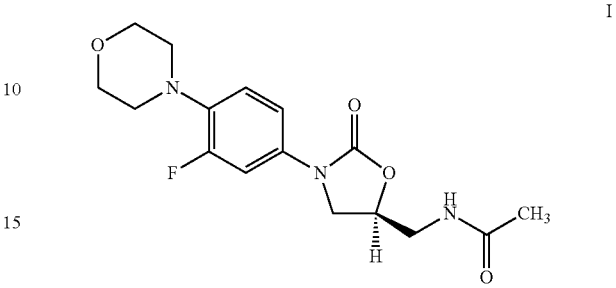

The main indications of linezolid are infections of the skin and soft tissues and pneumonia (particularly hospital-acquired pneumonia). Linezolid is marketed by Pfizer under the trade names Zyvox (in the United States, United Kingdom, Australia, and several other countries), Zyvoxid (in Europe), and Zyvoxam (in Canada and Mexico).

The synthesis of Linezolid was first described in the US'792 patent. According to the US'792 patent, the Linezolid is prepared by a process as depicted in scheme 1:

Scheme-1:

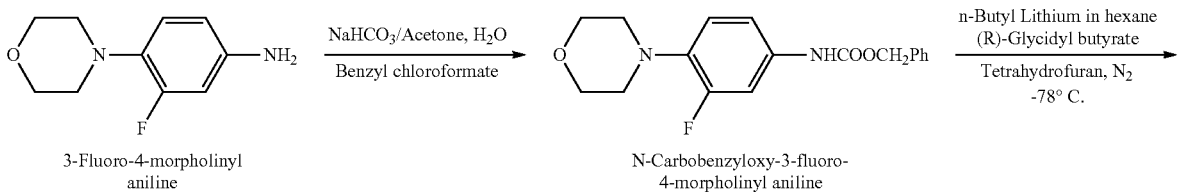

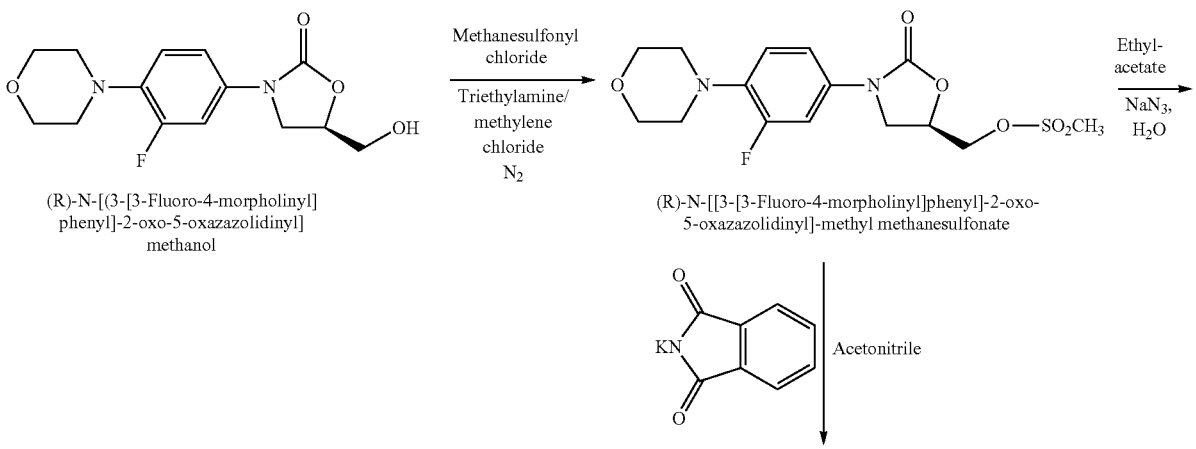

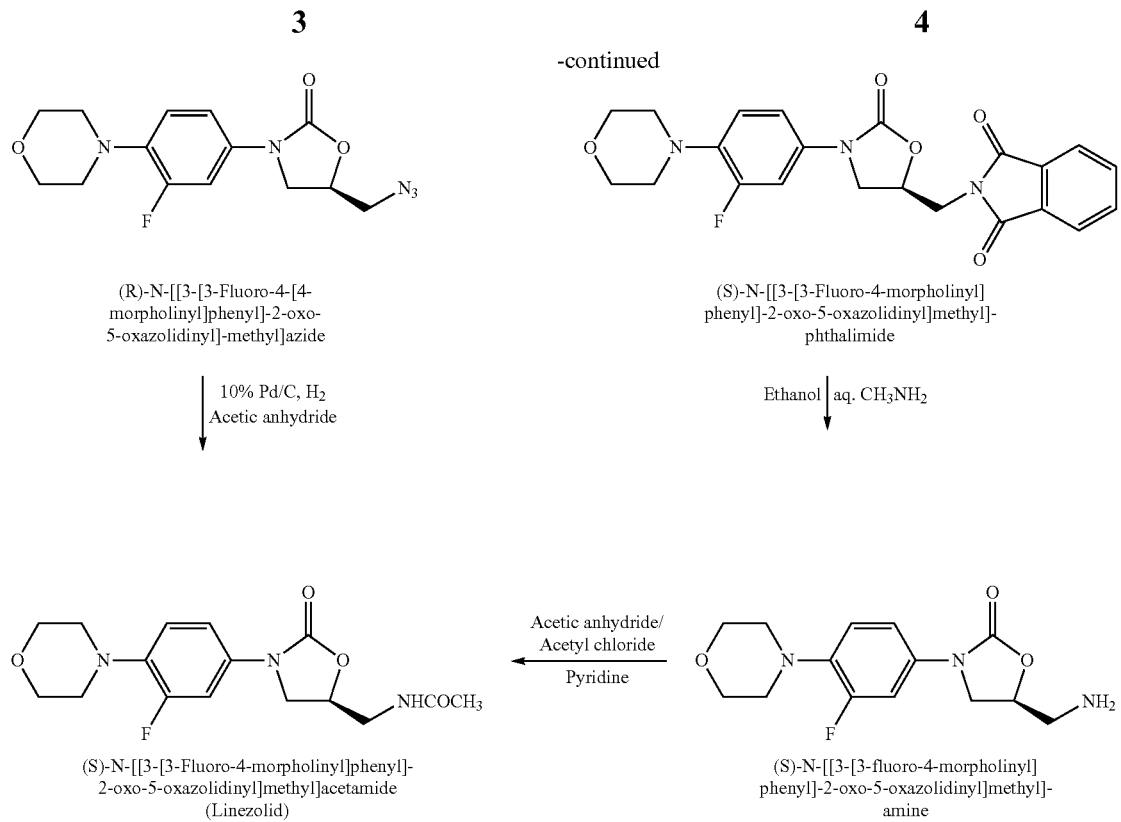

The synthesis of Linezolid as described in the US'792 patent involves the following main reaction steps: a) 3-Fluoro-4-morpholinyl aniline is reacted with benzyl chloroformate in the presence of sodium bicarbonate to produce N-carbobenzyloxy-3-fluoro-4-morpholinyl aniline; b) the N-carbobenzyloxy-3-fluoro-4-morpholinyl aniline is reacted with a solution of (R)-glycidyl butyrate in tetrahydrofuran in the presence of n-butyl lithium/hexane at a temperature of −78° C. under nitrogen atmosphere, followed by tedious work-up and isolation methods to produce the (5R)-5-(hydroxymethyl)-3-[3-fluoro-4-(4-morpholinyl)phenyl]-2-oxazolidinone; c) the (5R)-5-(Hydroxymethyl)-3-[3-fluoro-4-(4-morpholinyl)phenyl]-2-oxazolidinone is reacted with methanesulfonyl chloride in the presence of triethylamine in methylene chloride solvent under nitrogen atmosphere to produce (5R)-[[3-[3-fluoro-4-(4-morpholinyl)]phenyl]-2-oxo-5-oxazolidinyl]methyl methane sulfonate; d) (i) the (5R)-[[3-[3-fluoro-4-(4-morpholinyl)]phenyl]-2-oxo-5-oxazolidinyl]methyl methane sulfonate is reacted with sodium azide to produce (5R)-[[3-[3-fluoro-4-(4-morpholinyl)]phenyl]-2-oxo-5-oxazolidinyl]methyl azide, or alternatively (ii) the (5R)-[[3-[3-fluoro-4-(4-morpholinyl)]phenyl]-2-oxo-5-oxazolidinyl]methyl methane sulfonate intermediate is reacted with potassium phthalimide to produce (S)—N-[[3-[3-Fluoro-4-[4-morpholinyl]phenyl]-2-oxo-5-oxazolidinyl]methyl]phthalimide; e) (i) the (5R)-[[3-[3-fluoro-4-(4-morpholinyl)]phenyl]-2-oxo-5-oxazolidinyl]methyl azide intermediate is hydrogenated in the presence of 10% palladium/carbon to produce (S)—N-[[3-[3-Fluoro-4-[4-morpholinyl]phenyl]-2-oxo-5-oxazolidinyl]methyl]amine, or (ii) the (S)—N-[[3-[3-Fluoro-4-[4-morpholinyl]phenyl]-2-oxo-5-oxazolidinyl]methyl]phthalimide intermediate is then reacted with aqueous methyl amine to produce (S)—N-[3-fluoro-4-(4-morpholinyl)phenyl]-2-oxo-5-oxazolidinyl-methyl amine; and f) the (S)—N-[3-fluoro-4-(4-morpholinyl)phenyl]-2-oxo-5-oxazolidinyl-methyl amine intermediate is then subjected to acetylation with acetic anhydride to produce Linezolid.

The processes for the preparation of Linezolid as described in the aforementioned prior art suffer from several disadvantages and limitations. The main disadvantage of the prior art processes is that the reaction between N-carbobenzyloxy-3-fluoro-4-morpholinyl aniline and (R)-glycidyl butyrate in tetrahydrofuran in the presence of n-butyl lithium/hexane should be performed at extremely low temperatures (−78° C.) under very strict control of reaction conditions; processes involving extreme low temperatures are undesirable for large-scale operations since they require special equipment and an additional reactor, adding to the cost, thereby making the processes commercially unfeasible.

Various processes for the preparation of Linezolid, its intermediates, and related compounds are described in U.S. Pat. No. 5,837,870, U.S. Pat. No. 5,880,118, U.S. Pat. No. 6,107,519, U.S. Pat. No. 6,362,334, U.S. Pat. No. 6,887,995, U.S. Pat. No. 7,429,661, U.S. Pat. No. 7,307,163 and U.S. Pat. No. 7,291,614; PCT Publication Nos. WO 99/24393, WO 2007/116284, WO 2009/063505, WO 2010/031769, WO 2010/081404, WO 2010/084514, WO 2011/077,310, WO 2011/137222 and WO 2012/114355; Chinese Patent Application Publication No. CN 1772750; and Journal Articles: J. Med. Chem. 39(3), 673-679, 1996; Tetrahedron Lett., 40(26), 4855, 1999; and Organic Letters 2003, 5, 963-965.

According to the U.S. Pat. No. 5,837,870 (hereinafter referred to as the US'870 patent), the Linezolid is prepared by a process as depicted in scheme 2:

Scheme-2:

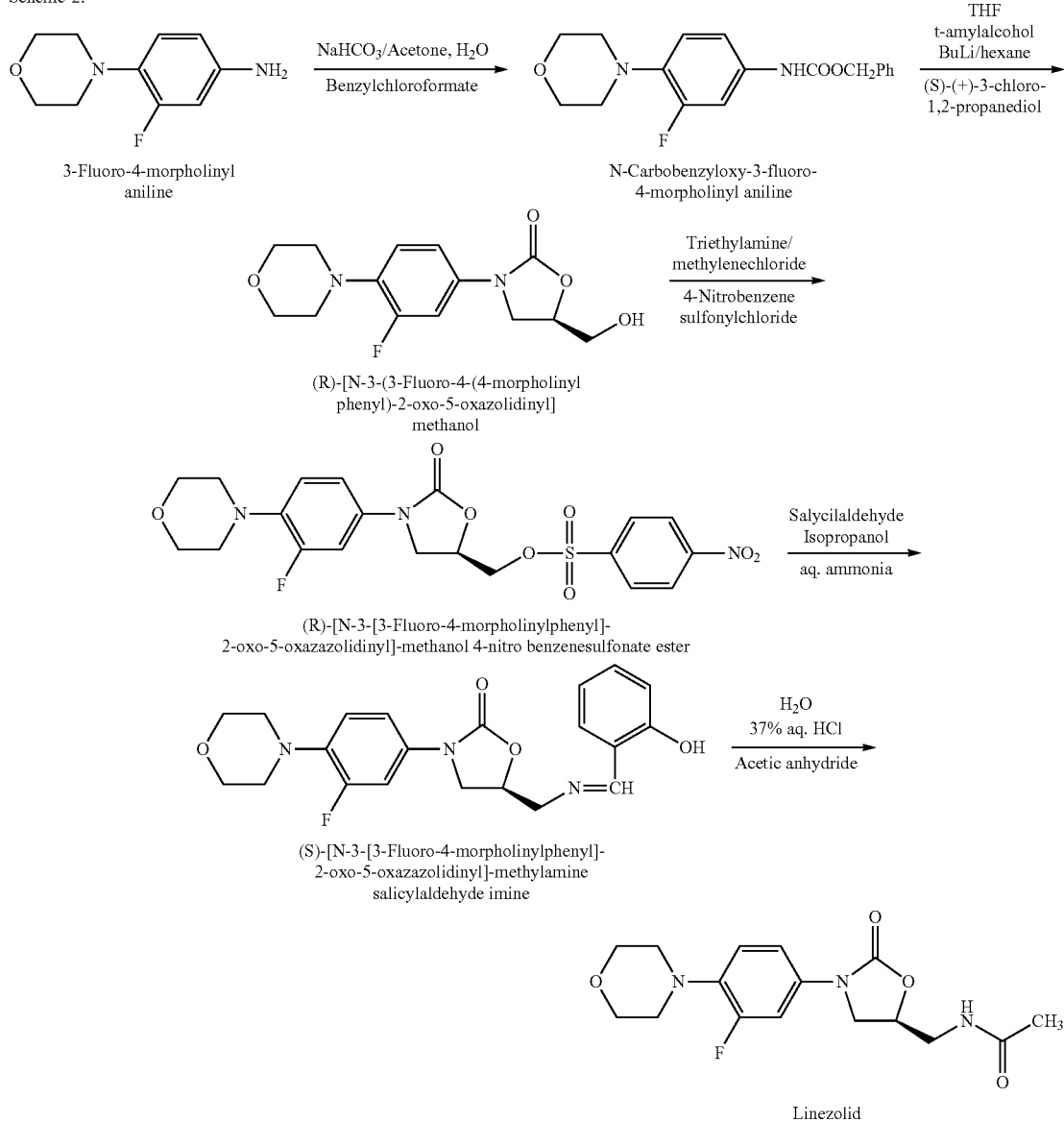

As stated in the preceding paragraphs, the processes for the preparation of Linezolid as disclosed in the prior art were tedious and cumbersome—for example, U.S. Pat. No. 5,837,870 describes a process for the preparation of (5R)-5-(hydroxymethyl)-3-[3-fluoro-4-(4-morpholinyl)phenyl]-2-oxazolidinone intermediate wherein, tetrahydrofuran is mixed with t-amyl alcohol, followed by the addition of butyl lithium in hexanes with agitation to produce a lithium t-amylate mixture, which is then added to solution of N-carbobenzyloxy-3-fluoro-4-morpholinyl aniline [obtained as per the process described in J. Med. Chem., 39(3), 673 (1996)] in tetrahydrofuran while maintaining the temperature at less than 8° C. and rinsed in with tetrahydrofuran to produce a lithium anion mixture. Tetrahydrofuran is mixed with S-(+)-3-chloro-1,2-propanediol, the resulting mixture is cooled to −16° C., followed by the addition of potassium t-butoxide in tetrahydrofuran while maintaining the temperature at less than −10° C. The resulting slurry is then stirred at −14° C. to 0° C. for 1 hour and then added to the lithium anion mixture while maintaining both mixtures at 0° C., then rinsed in with tetrahydrofuran. The resulting slurry is stirred for 2 hours at 20-23° C. and then cooled to 6° C., followed by the addition of a mixture of citric acid monohydrate in water. The resultant liquid phases are separated and the lower aqueous phase is washed with ethyl acetate. The organic layers are combined and solvent is removed under reduced pressure. Heptane and water are added to the resulting mass and the solvent is removed by reduced pressure until a total volume of 5 ml remains. The precipitated product is collected by vacuum filtration and washed with water and then dried in a stream of nitrogen to produce (5R)-5-(hydroxymethyl)-3-[3-fluoro-4-(4-morpholinyl)phenyl]-2-oxazolidinone.

Organic Letters 2003, 5, 963-965 describes a process for the preparation of Linezolid as depicted in scheme 3:

Scheme-3:
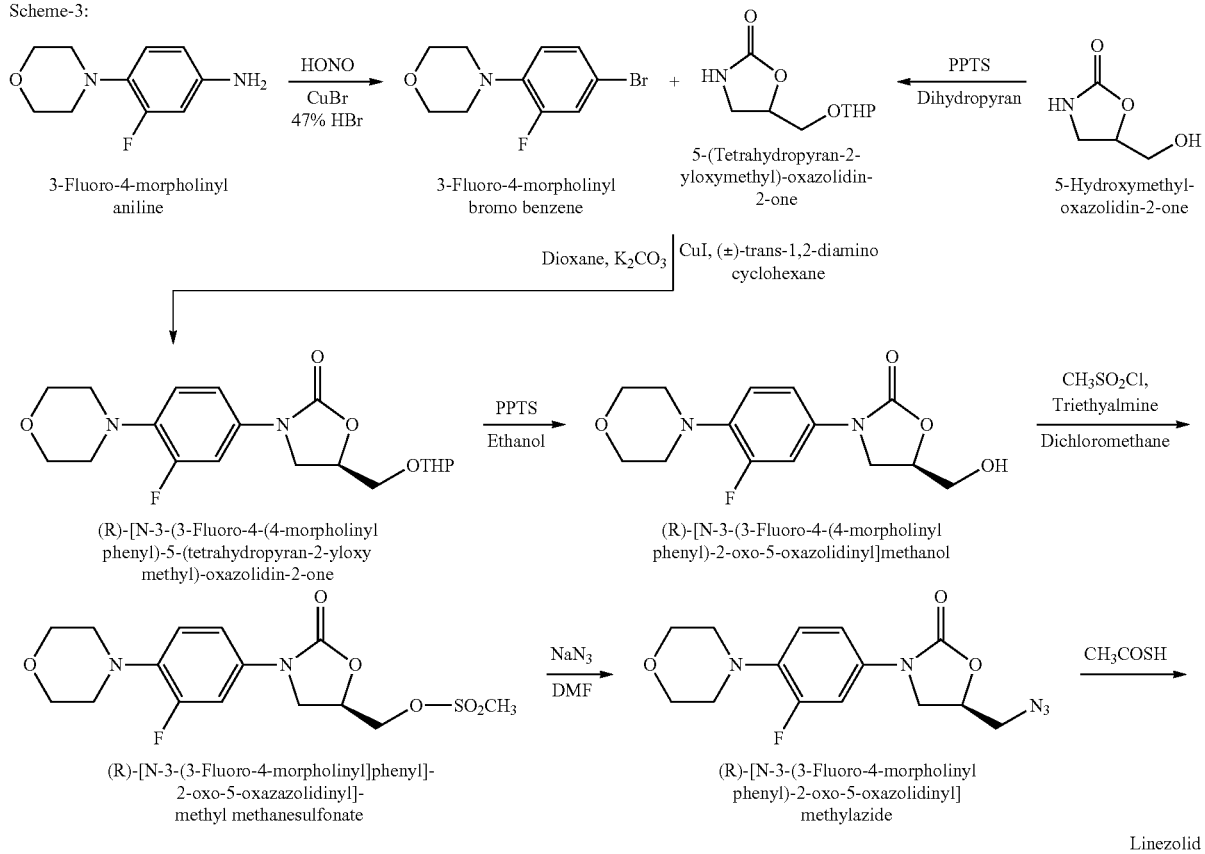
U.S. Pat. No. 6,107,519 (hereinafter referred to as the US'519 patent) describes various processes for the preparation of Linezolid as depicted in schemes 4 & 5:
Scheme-4:
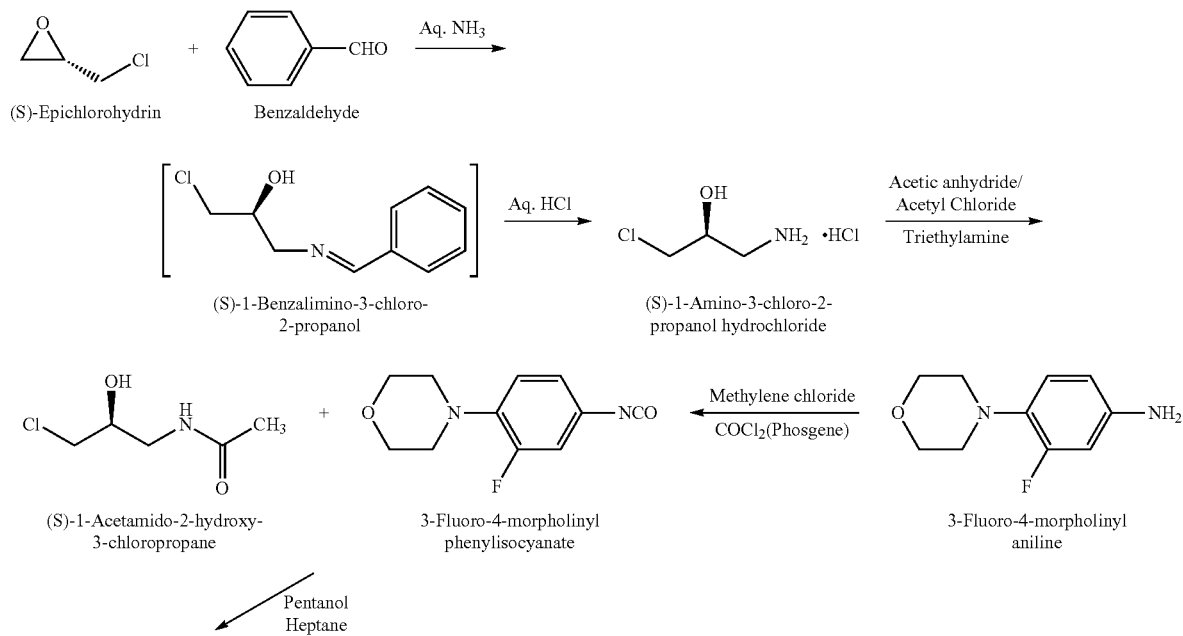

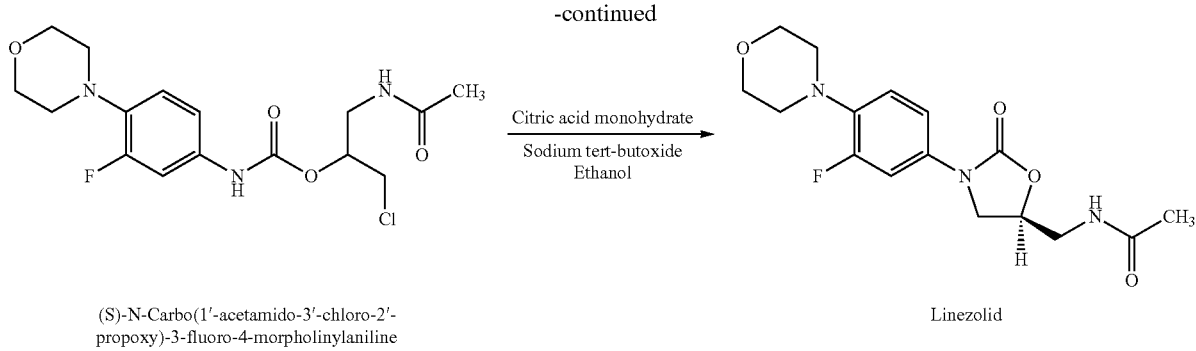
Scheme-5:
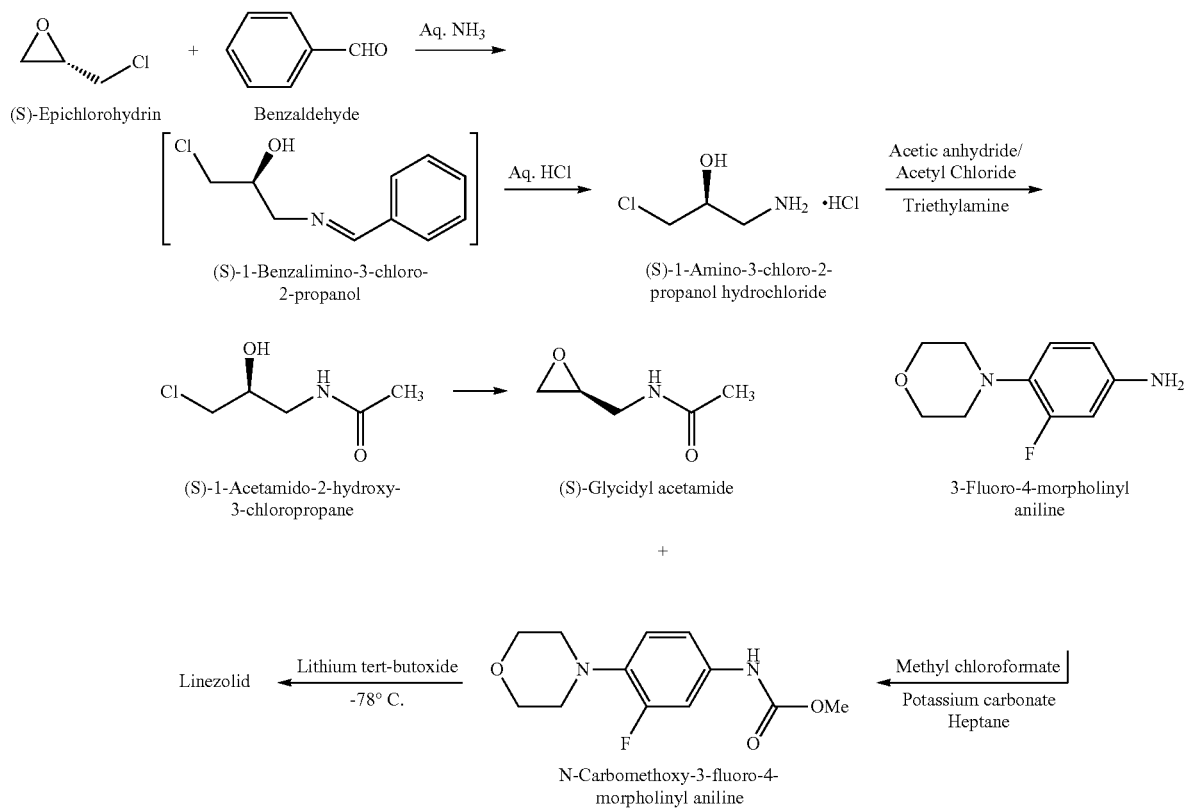
PCT Publication No. WO 2012/114355 describes a process for the preparation of Linezolid as depicted in scheme 6:
Scheme 6:
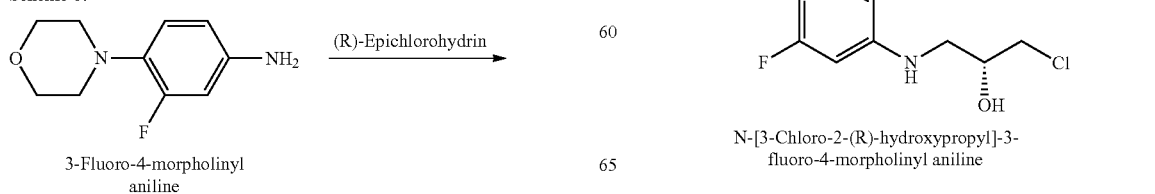

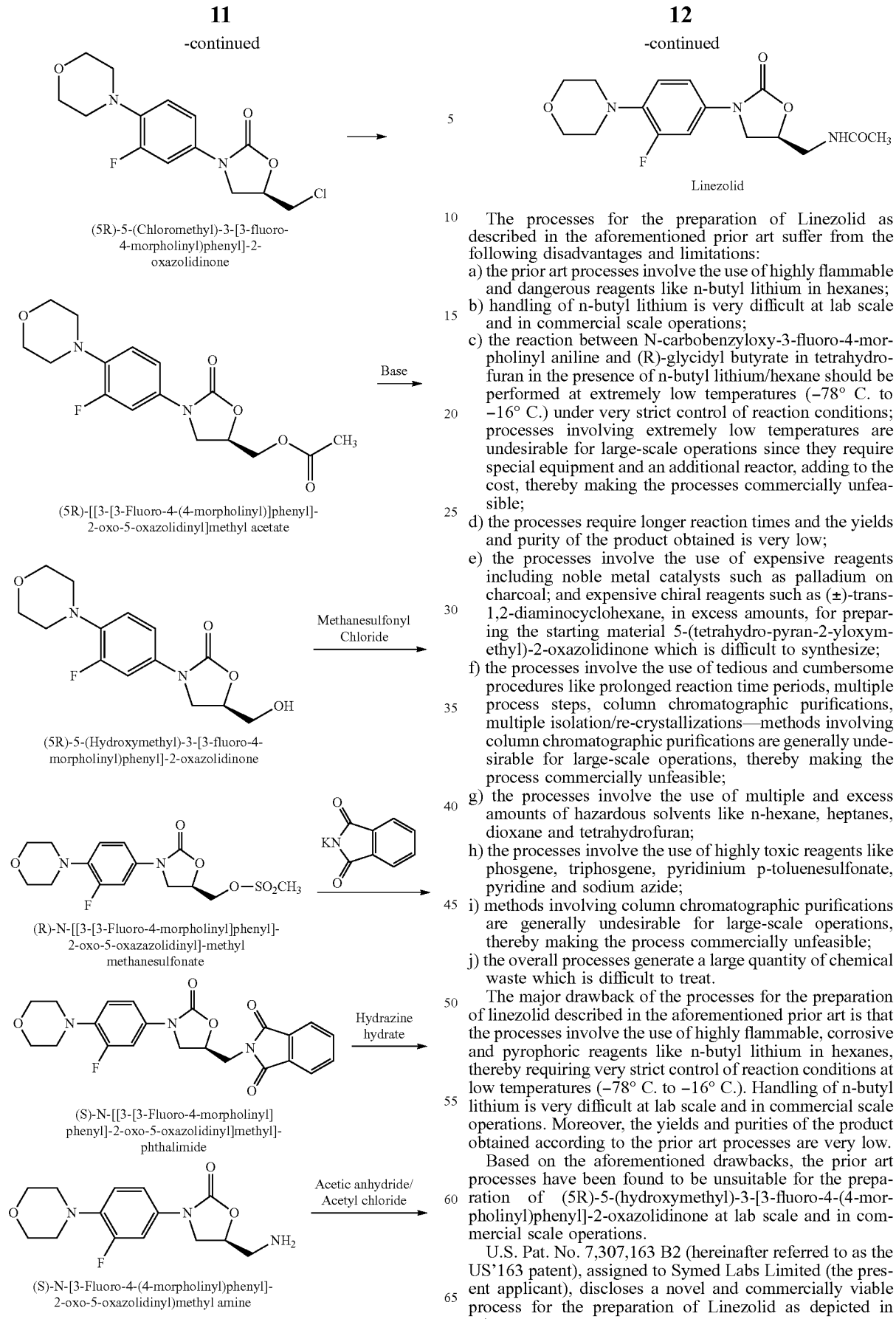

The processes for the preparation of Linezolid as described in the aforementioned prior art suffer from the following disadvantages and limitations:
a) the prior art processes involve the use of highly flammable and dangerous reagents like n-butyl lithium in hexanes;
b) handling of n-butyl lithium is very difficult at lab scale and in commercial scale operations;
c) the reaction between N-carbobenzyloxy-3-fluoro-4-morpholinyl aniline and (R)-glycidyl butyrate in tetrahydrofuran in the presence of n-butyl lithium/hexane should be performed at extremely low temperatures (−78° C. to −16° C.) under very strict control of reaction conditions; processes involving extremely low temperatures are undesirable for large-scale operations since they require special equipment and an additional reactor, adding to the cost, thereby making the processes commercially unfeasible;
d) the processes require longer reaction times and the yields and purity of the product obtained is very low;
e) the processes involve the use of expensive reagents including noble metal catalysts such as palladium on charcoal; and expensive chiral reagents such as (±)-trans-1,2-diaminocyclohexane, in excess amounts, for preparing the starting material 5-(tetrahydro-pyran-2-yloxymethyl)-2-oxazolidinone which is difficult to synthesize;
f) the processes involve the use of tedious and cumbersome procedures like prolonged reaction time periods, multiple process steps, column chromatographic purifications, multiple isolation/re-crystallizations—methods involving column chromatographic purifications are generally undesirable for large-scale operations, thereby making the process commercially unfeasible;
g) the processes involve the use of multiple and excess amounts of hazardous solvents like n-hexane, heptanes, dioxane and tetrahydrofuran;
h) the processes involve the use of highly toxic reagents like phosgene, triphosgene, pyridinium p-toluenesulfonate, pyridine and sodium azide;
i) methods involving column chromatographic purifications are generally undesirable for large-scale operations, thereby making the process commercially unfeasible;
j) the overall processes generate a large quantity of chemical waste which is difficult to treat.

The major drawback of the processes for the preparation of linezolid described in the aforementioned prior art is that the processes involve the use of highly flammable, corrosive and pyrophoric reagents like n-butyl lithium in hexanes, thereby requiring very strict control of reaction conditions at low temperatures (−78° C. to −16° C.). Handling of n-butyl lithium is very difficult at lab scale and in commercial scale operations. Moreover, the yields and purities of the product obtained according to the prior art processes are very low.

Based on the aforementioned drawbacks, the prior art processes have been found to be unsuitable for the preparation of (5R)-5-(hydroxymethyl)-3-[3-fluoro-4-(4-morpholinyl)phenyl]-2-oxazolidinone at lab scale and in commercial scale operations.

U.S. Pat. No. 7,307,163 B2 (hereinafter referred to as the US'163 patent), assigned to Symed Labs Limited (the present applicant), discloses a novel and commercially viable process for the preparation of Linezolid as depicted in scheme 7:

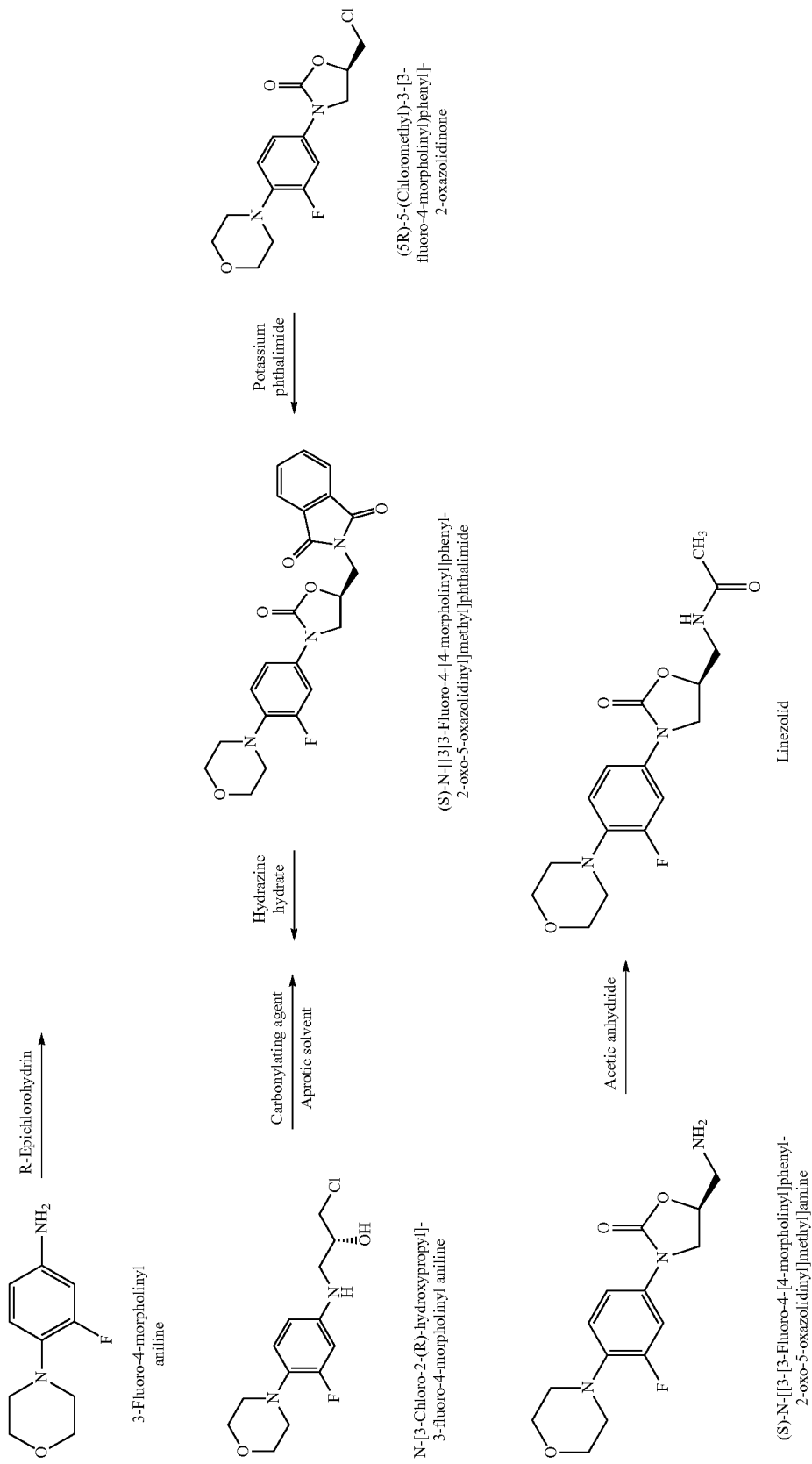

U.S. Pat. No. 7,429,661 B2 (hereinafter referred to as the US'661 patent), assigned to Symed Labs Limited (the present applicant), discloses a novel and commercially viable process for the preparation of Linezolid as depicted in scheme 8:

Scheme-8:

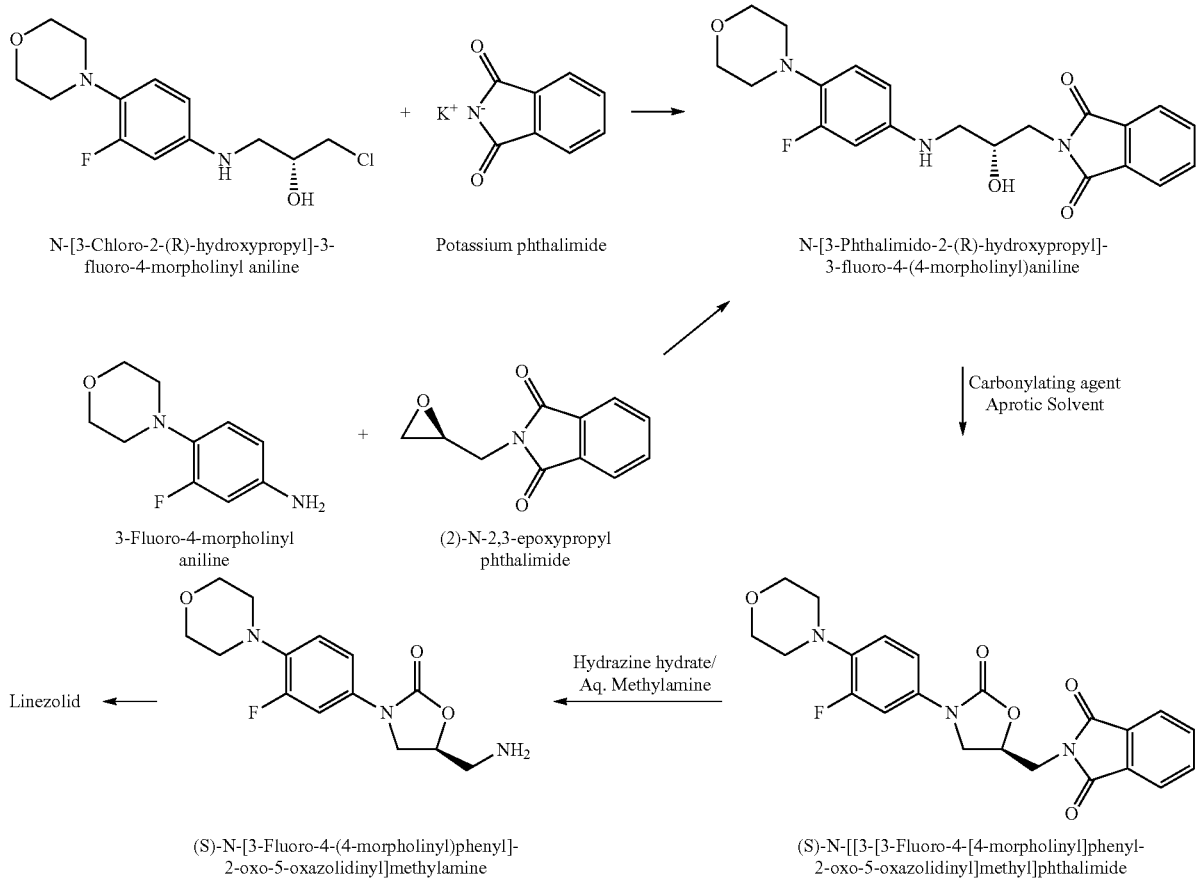

However, a need remains for an improved, commercially viable, cost effective and environmentally friendly process of preparing Linezolid with high yield and purity, to resolve the problems associated with the processes described in the prior art, and that will be suitable for large-scale preparation. Desirable process properties include non-hazardous conditions, environmentally friendly and easy to handle reagents, reduced cost, greater simplicity, increased purity, and increased yield of the product, thereby enabling the production of Linezolid, in high purity and with high yield.

SUMMARY OF THE INVENTION

The present inventors have surprisingly and unexpectedly found that Linezolid can be prepared in high purity and with high yield, by reacting N-[3-phthalimido-2-(R)-hydroxypropyl]-3-fluoro-4-(4-morpholinyl)aniline with an alkyl or aryl chloroformate, or a dicarbonate reagent, in the presence of a base to produce an alkyl/aryl N-[3-phthalimido-2-(R)-hydroxypropyl]-N-[3-fluoro-4-(4-morpholinyl)phenyl]-carbamate intermediate, which is then reacted with an acetylating agent to produce an alkyl/aryl N-[3-phthalimido-2-(R)-acetyloxypropyl]-N-[3-fluoro-4-(4-morpholinyl) phenyl]-carbamate, followed by deprotection with a suitable reagent in the presence of a base to produce linezolid.

In one aspect, provided herein are efficient, industrially advantageous and environmentally friendly processes for the preparation of linezolid, in high yield and with high purity, using novel intermediates. The processes disclosed herein avoid the tedious and cumbersome procedures of the prior processes, thereby resolving the problems associated with the processes described in the prior art, which is more convenient to operate at lab scale and in commercial scale operations.

In another aspect, provided herein is a novel (R)-phthalimido-2-acetyloxypropyl-carbamate compound of formula III:

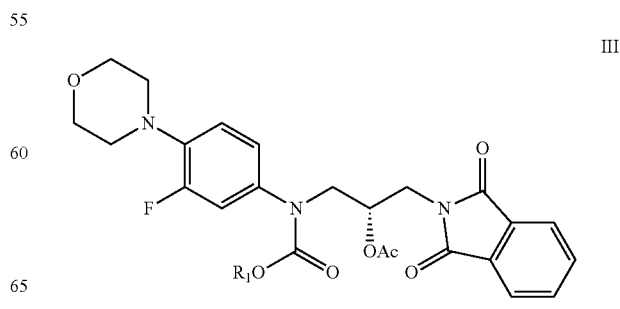

III or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

In another aspect, provided herein is a novel (R)-phthalimido-2-hydroxypropyl-carbamate compound of formula IV:

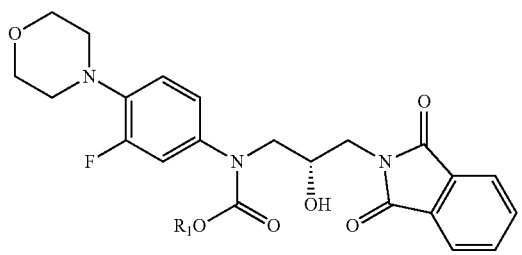

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl.

In another aspect, provided herein is a novel (R)-amino-2-acetyloxypropyl-carbamate compound of formula V:

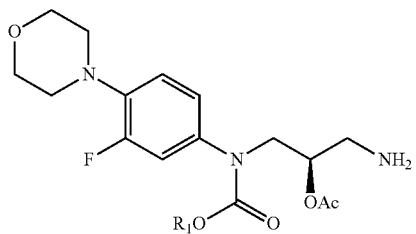

V or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

In another aspect, provided herein is a novel (R)-amino-2-hydroxypropyl-carbamate compound of formula VI:

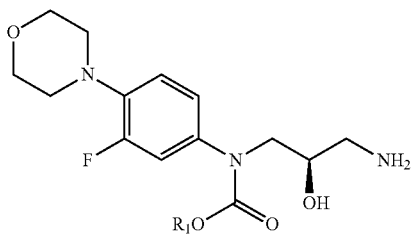

VI or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl.

In another aspect, provided herein is a novel (R)-2-hydroxypropyl-carbamate compound of formula VII:

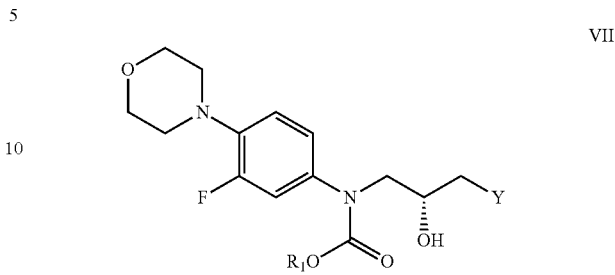

VII or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and Y is a leaving group such as a halogen or a sulfonyloxy group.

In another aspect, provided herein is a novel (R)-2-acetyloxypropyl-carbamate compound of formula VIII:

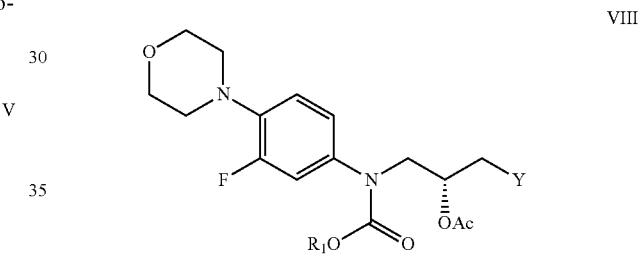

VIII or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; Y is a leaving group such as a halogen or a sulfonyloxy group, and 'Ac' represents an acetyl group.

In another aspect, provided herein is a novel (R)-2,3-epoxypropyl-carbamate compound of formula IX:

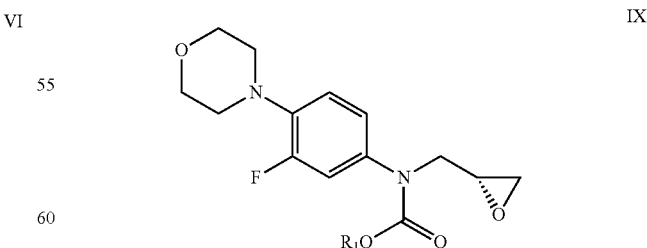

IX or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl.

In another aspect, provided herein is a novel N-[2(R)-2,3-epoxypropyl]-3-fluoro-4-(4-morpholinyl)aniline of formula X:

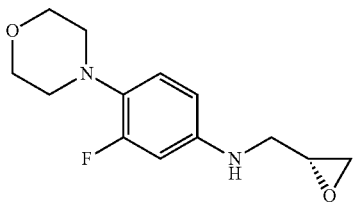

X or an enantiomeric form or a mixture of enantiomeric forms thereof, or a salt thereof.

In another aspect, provided herein is a novel (R)-acetamido-2-hydroxypropyl-carbamate compound of formula XI:

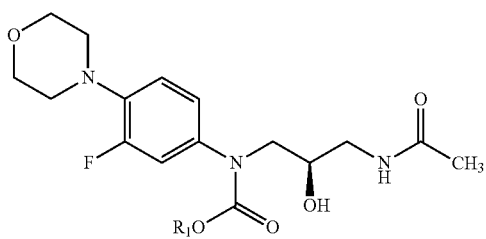

XI or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl.

In another aspect, provided herein is a novel (R)-acetamido-2-acetyloxypropyl-carbamate compound of formula XII:

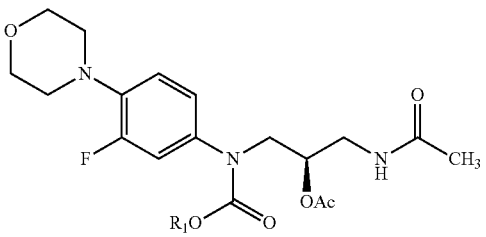

XII or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

In another aspect, the present invention also encompasses the use of the novel compounds of formula III, IV, V, VI, VII, VIII, IX, X, XI and XII disclosed herein for preparing Linezolid.

The processes for the preparation of Linezolid disclosed herein have the following advantages over the processes described in the prior art:

i) the processes involve the use of novel intermediate compounds;

ii) the overall process involves a reduced number of process steps, shorter reactions times and less expensive reagents thereby making the process cost effective;

iii) the overall yield of the Linezolid product is increased and the purity of the product is increased without additional purifications such as multiple isolations and re-crystallizations or column chromatographic purifications;

iv) the processes avoid the use of highly inflammable, dangerous and difficult to handle reagents like n-butyl lithium;

v) the processes avoid the use of highly inflammable and toxic solvents like hexane, dioxane and heptanes;

vi) the processes avoid the use of additional and excess amounts of solvents, multiple isolation steps, column chromatographic purifications;

vii) the processes avoid the use of expensive reagents including noble metal catalysts, e.g., palladium on charcoal, chiral reagents like (±)-trans-1,2-diaminocyclohexane and 5-(tetrahydro-pyran-2-yloxymethyl)-2-oxazolidinone;

viii) the process avoids the use of tedious and cumbersome procedures like prolonged reaction time periods, extremely low temperatures (−78° C. to −16° C.), multiple process steps, column chromatographic purifications, multiple isolations, additional and excess amounts of solvents; and ix) the process involves easy work-up methods and simple isolation processes, and there is a reduction in chemical waste.

In a preferred embodiment, the radical $R_1$ in the compounds of formulae III, IV, V, VI, VII, VIII, IX, XI and XII is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

In another preferred embodiment, the leaving group Y in the compound of formula VII & VIII is a halogen, or an alkyl or aryl sulfonyloxy group. Specifically, the leaving group Y is selected from the group consisting of Cl, Br, I, methanesulfonyloxy, toluenesulfonyloxy and trifluoromethanesulfonyloxy group; more specifically the leaving group Y is Cl or toluenesulfonyloxy; and a most specific leaving group is Cl.

The processes for the preparation of Linezolid using novel intermediates disclosed herein may be represented by a schematic diagram as depicted in scheme-9:

Schematic Representation:
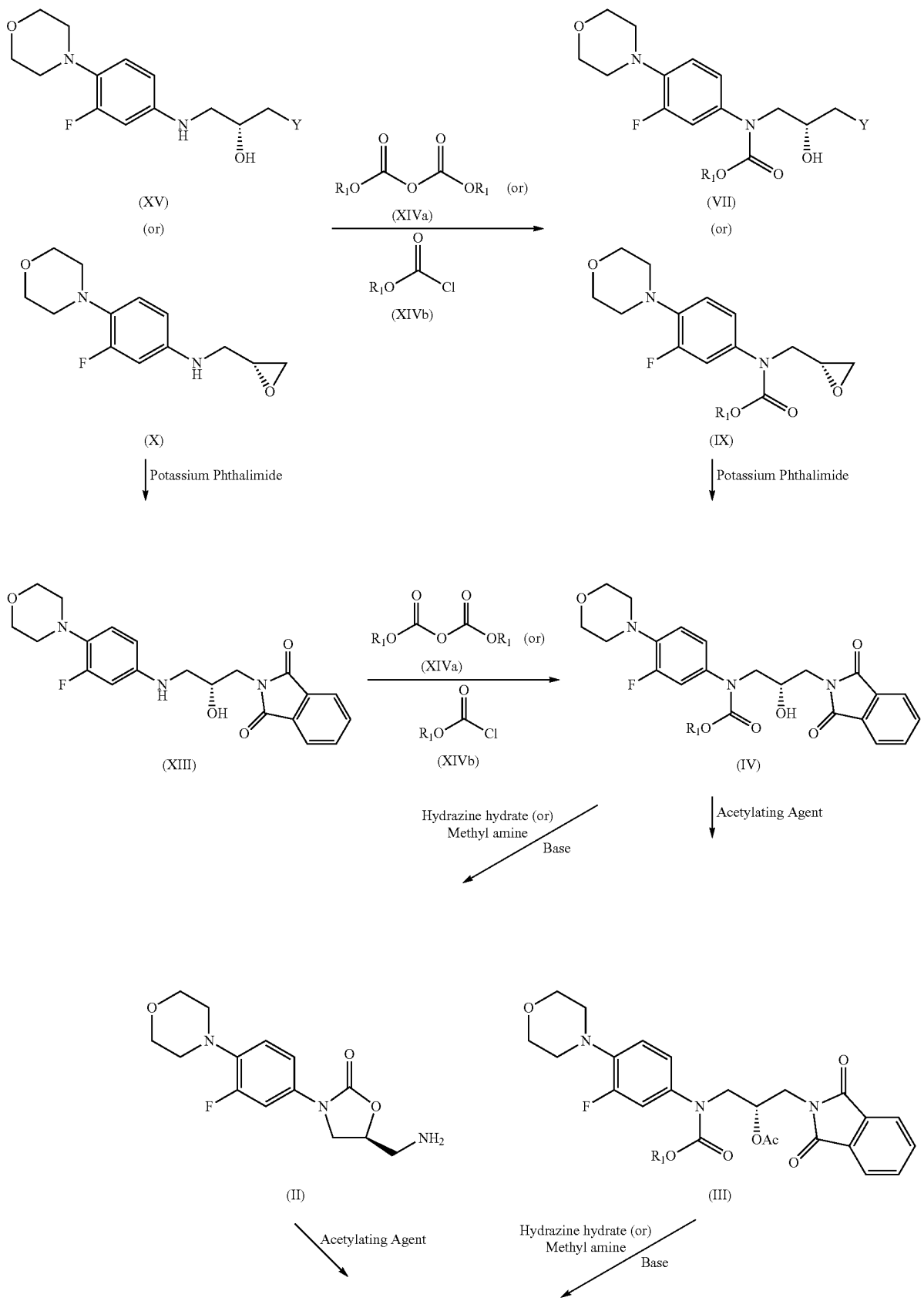

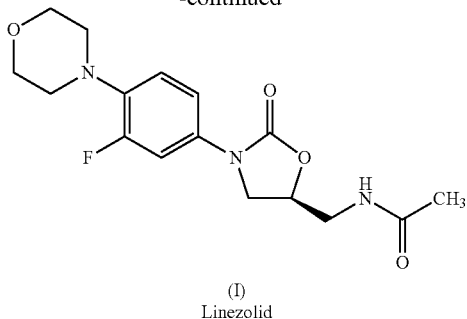

(I)
Linezolid

DETAILED DESCRIPTION OF THE INVENTION

According to one aspect, there is provided an improved and cost effective process for the preparation of Linezolid of formula I:

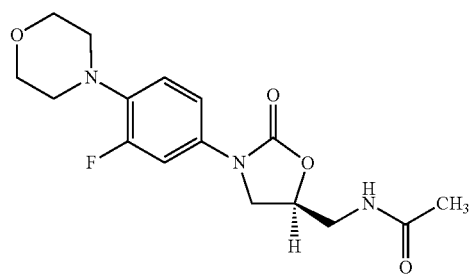

I or an enantiomeric form or a mixture of enantiomeric forms thereof, which comprises:

a) acetylating (R)-phthalimido-2-hydroxypropyl-carbamate compound of formula IV:

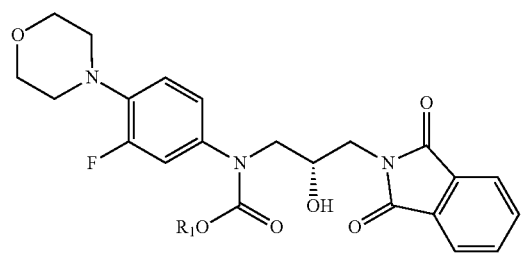

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl;

with an acetylating agent optionally in the presence of a base to produce an (R)-phthalimido-2-acetyloxypropyl-carbamate compound of formula III:

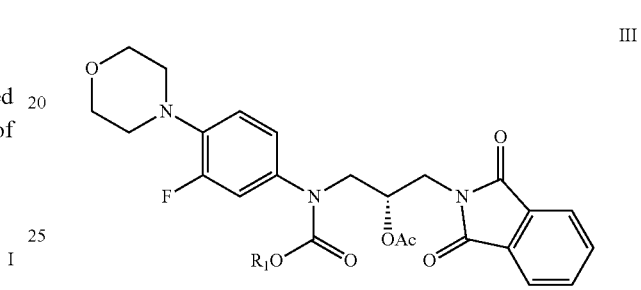

III or an enantiomeric form or a mixture of enantiomeric forms thereof, wherein $R_1$ is as defined in formula IV, and 'Ac' represents an acetyl group; and b) reacting the (R)-phthalimido-2-acetyloxypropyl-carbamate compound of formula III with a suitable reagent, optionally in the presence of a base, to produce the Linezolid of formula I.

The structural formulae of novel intermediate compounds disclosed herein contain one chiral centre and thus exist as two optical isomers, i.e. enantiomers (R & S-isomers). The process disclosed herein encompasses the preparation of both enantiomers and mixtures thereof in all proportions.

In one embodiment, the radical $R_1$ in the compounds of formulae III and IV is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

Unless otherwise specified, the term "alkyl", as used herein, denotes an aliphatic hydrocarbon group which may be straight or branched having 1 to 12 carbon atoms in the chain. Preferred alkyl groups have 1 to 6 carbon atoms in the chain. The alkyl may be substituted with one or more "cycloalkyl groups". Exemplary alkyl groups include methyl, ethyl, n-propyl, iso-propyl, n-butyl, iso-butyl, t-butyl, and n-pentyl.

The term "cycloalkyl", as used herein, denotes a non-aromatic mono- or multicyclic ring system of 3 to 10 carbon atoms, preferably of about 5 to about 10 carbon atoms. Exemplary monocyclic cycloalkyl groups include cyclopentyl, cyclohexyl, cycloheptyl and the like.

The term "aralkyl", as used herein, denotes an aryl-alkyl group wherein the aryl and alkyl are as herein described. Preferred aralkyls contain a lower alkyl moiety. Exemplary aralkyl groups include benzyl, 2-phenethyl and naphthalenemethyl.

The term "aryl", as used herein, denotes an aromatic monocyclic or multicyclic ring system of 6 to 10 carbon atoms. The aryl is optionally substituted with one or more "ring system substituents" which may be the same or different, and are as defined herein. Exemplary aryl groups include phenyl, tolyl or naphthyl.

The compounds of formulae III & IV disclosed herein are novel and constitute another aspect of the present invention.

The use of the novel intermediate compounds of formulae III & IV in the preparation of Linezolid of formula I is novel and forms further aspect of the present invention.

Advantageously, the novel intermediate compounds of Linezolid disclosed herein are obtained as solid state forms in substantially pure form.

The term "substantially pure" as used herein refers to the solid state form of linezolid intermediates, disclosed herein, having a purity of greater than about 90 wt %, specifically greater than about 95 wt %, more specifically greater than about 98 wt %, and still more specifically greater than about 99 wt %. The purity is preferably measured by High Performance. Liquid Chromatography (HPLC). For example, the purity of solid state form of linezolid intermediates obtained by the processes disclosed herein can be about 95% to about 99%, or about 98% to about 99.9%, as measured by HPLC.

Unless otherwise specified, the term 'salt' as used herein may include acid addition salts and base addition salts.

Acid addition salts, as used herein, include the salts that are derived from organic and inorganic acids. For example, the acid addition salts are derived from a therapeutically acceptable acid such as hydrochloric acid, hydrobromic acid, sulfuric acid, nitric acid, oxalic acid, acetic acid, propionic acid, phosphoric acid, succinic acid, maleic acid, fumaric acid, citric acid, glutaric acid, tartaric acid, benzenesulfonic acid, toluenesulfonic acid, di-p-toluoyl-L-(+)-tartaric acid, malic acid, ascorbic acid, and the like.

Base addition salts may be derived from an organic or an inorganic base. For example, the base addition salts are derived from alkali or alkaline earth metals such as sodium, calcium, potassium and magnesium; ammonium salt, organic amines such as ethylamine, tert-butylamine, diethylamine, diisopropylamine, and the like. Exemplary acetylating agents used in step-(a) include, but are not limited to, acetyl halide such as acetyl chloride, acetyl bromide, acetyl iodide; acetic anhydride, sodium acetate, and the like, or a combination thereof. A most specific acetylating agent is acetic anhydride.

The reaction in step-(a) can be carried out in the presence or absence of a reaction inert solvent. In one embodiment, the reaction in step-(a) is carried out in the absence of a solvent. In another embodiment, the reaction in step-(a) is optionally carried out in the presence of a first solvent. The term solvent also includes mixture of solvents.

Exemplary first solvents used in step-(a) include, but are not limited to, water, an alcohol, a hydrocarbon solvent, an ester, a ketone, an ether, a nitrile, a polar aprotic solvent, a halogenated hydrocarbon solvent, and mixtures thereof.

Specifically, the first solvent used in step-(a) is selected from the group consisting of water, methanol, ethanol, isopropanol, n-butanol, ethyl acetate, methyl acetate, isopropyl acetate, tert-butyl methyl acetate, ethyl formate, acetone, n-pentane, n-hexane, n-heptane, cyclohexane, toluene, xylene, tetrahydrofuran, 2-methyl-tetrahydrofuran, dioxane, diethyl ether, diisopropyl ether, methyl tert-butyl ether, monoglyme, diglyme, acetonitrile, propionitrile, N,N-dimethylformamide, N,N-dimethylacetamide, dimethylsulfoxide, dichloromethane, dichloroethane, and mixtures thereof. Most specific first solvents are methanol, ethanol, isopropanol, and mixtures thereof.

In one embodiment, the acetylating agent in step-(a) is used in a ratio of about 1 to 6 equivalents, specifically about 3 to 5 equivalents, with respect to (R)-phthalimido-2-hydroxypropyl-carbamate compound of formula IV in order to ensure a proper course of the reaction.

In another embodiment, the acetylation in step-(a) is optionally carried out in the presence of a base. Specifically, the base is an organic base or inorganic base, and most specifically an inorganic base.

Exemplary bases include, but are not limited to, hydroxides, alkoxides, bicarbonates, phosphates and carbonates of alkali or alkaline earth metals; ammonia, collidine, trimethylamine, triethylamine, tributylamine, diisopropylethylamine, N-methylmorpholine, 1-alkylimidazole and 1,8-diazabicyclo[5.4.0]undec-7-ene (DBU). Specific bases are aqueous ammonia, potassium phosphate, sodium hydroxide, calcium hydroxide, magnesium hydroxide, potassium hydroxide, sodium carbonate, potassium carbonate, sodium bicarbonate, potassium bicarbonate, sodium tert-butoxide, sodium isopropoxide, potassium tert-butoxide, or a combination thereof; and most specifically potassium carbonate, sodium hydroxide and potassium hydroxide.

The reaction temperature and time period will ordinarily depend on the starting compounds and the solvent/reagent employed in the reaction.

In one embodiment, the acetylation reaction in step-(a) is carried out at a temperature of about 0° C. to the reflux temperature of the solvent used, specifically at a temperature of about 25° C. to the reflux temperature of the solvent used, and more specifically at about 30° C. to about 60° C. The reaction time may vary between about 1 hour to about 10 hours, specifically about 2 hours to about 7 hours, and more specifically about 4 hours to about 6 hours.

The reaction mass containing the (R)-phthalimido-2-acetyloxypropyl-carbamate compound of formula III obtained in step-(a) may be subjected to usual work up such as a washing, an extraction, a pH adjustment, an evaporation, a layer separation, a decolorization, or a combination thereof. The reaction mass may be used directly in the next step to produce the Linezolid of formula I, or the compound of formula III may be isolated and/or recrystallized and then used in the next step. After completion of the reaction, the excess acetic anhydride may be removed by distillation.

In one embodiment, the (R)-phthalimido-2-acetyloxypropyl-carbamate compound of formula III is isolated and/or re-crystallized from a suitable solvent by conventional methods such as cooling, seeding, partial removal of the solvent from the solution, by adding an anti-solvent to the solution, evaporation, vacuum distillation, or a combination thereof.

The solvent used for isolating and/or recrystallizing the (R)-phthalimido-2-acetyloxypropyl-carbamate compound of formula III is selected from the group consisting of water, an alcohol, a ketone, an ether, an ester, a hydrocarbon solvent, a halogenated hydrocarbon, and mixtures thereof. Specifically, the solvent is selected from the group consisting of water, methanol, ethanol, n-propanol, isopropyl alcohol, acetone, tetrahydrofuran, 2-methyl-tetrahydrofuran, diisopropyl ether, methyl tert-butyl ether, ethyl acetate, n-pentane, n-hexane, n-heptane, cyclohexane, toluene, xylene, dichloromethane, dichloroethane, chloroform, and mixtures thereof.

In one embodiment, a most specific (R)-phthalimido-2-acetyloxypropyl-carbamate compound of formula III prepared by the process described herein is N-[3-phthalimido-2-(R)-acetyloxypropyl]-N-[3-fluoro-4-(4-morpholinyl) phenyl]-carbamic acid ethyl ester of formula IIIa (formula III, wherein $R_1$ is ethyl):

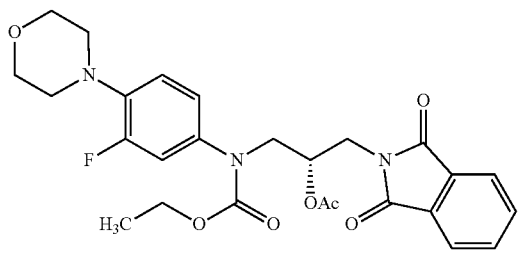

IIIa or an enantiomeric form or a mixture of enantiomeric forms thereof.

In another embodiment, a most specific (R)-phthalimido-2-acetyloxypropyl-carbamate compound of formula III prepared by the process described herein is N-[3-phthalimido-2-(R)-acetyloxypropyl]-N-[3-fluoro-4-(4-morpholinyl)phenyl]-carbamic acid tert-butyl ester of formula IIIb (formula III, wherein $R_1$ is tert-butyl):

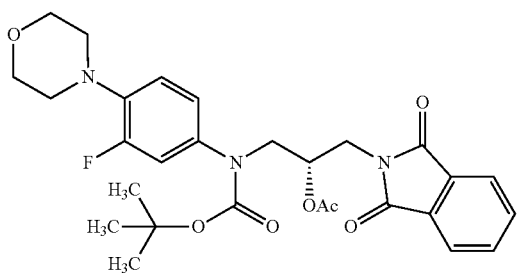

IIIb or an enantiomeric form or a mixture of enantiomeric forms thereof.

In another embodiment, a most specific (R)-phthalimido-2-acetyloxypropyl-carbamate compound of formula III prepared by the process described herein is N-[3-phthalimido-2-(R)-acetyloxypropyl]-N-[3-fluoro-4-(4-morpholinyl)phenyl]-carbamic acid benzyl ester of formula IIIc (formula III, wherein $R_1$ is benzyl):

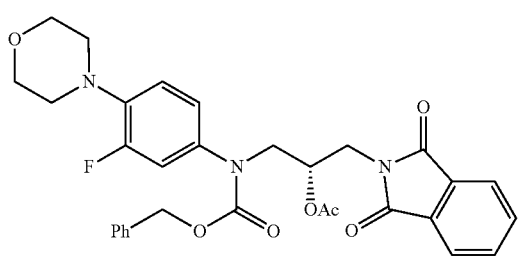

IIIc or an enantiomeric form or a mixture of enantiomeric forms thereof.

The reagent used in step-(b) is a primary amine formation agent. Exemplary primary amine formation agents used in step-(b) include, but are not limited to, hydrazine hydrate, methyl amine, and the like. A most specific reagent is hydrazine hydrate or aqueous methyl amine.

In another embodiment, the reaction in step-(b) is optionally carried out in the presence of a base. Specifically, the base is an organic or inorganic base, and most specifically an inorganic base, selected from the group as described hereinabove.

Specific bases are aqueous ammonia, sodium hydroxide, calcium hydroxide, magnesium hydroxide, potassium hydroxide, sodium carbonate, potassium carbonate, sodium bicarbonate, potassium bicarbonate, sodium tert-butoxide, sodium isopropoxide and potassium tert-butoxide; and most specifically potassium carbonate.

In one embodiment, the reaction in step-(b) is carried out in the presence of a second solvent.

Exemplary second solvents used in step-(b) include, but are not limited to, water, an alcohol, a hydrocarbon solvent, an ester, a ketone, an ether, a nitrile, a polar aprotic solvent, a halogenated hydrocarbon solvent, and mixtures thereof.

Specifically, the second solvent used in step-(b) is selected from the group consisting of water, methanol, ethanol, isopropanol, n-butanol, ethyl acetate, methyl acetate, isopropyl acetate, tert-butyl methyl acetate, ethyl formate, acetone, n-pentane, n-hexane, n-heptane, cyclohexane, toluene, xylene, tetrahydrofuran, 2-methyl-tetrahydrofuran, dioxane, diethyl ether, diisopropyl ether, methyl tert-butyl ether, monoglyme, diglyme, acetonitrile, propionitrile, N,N-dimethylformamide, N,N-dimethylacetamide, dimethylsulfoxide, dichloromethane, dichloroethane, and mixtures thereof. Most specific second solvents are methanol, ethanol, isopropanol, acetone, and mixtures thereof.

In one embodiment, the reagent in step-(b) is used in a ratio of about 1 to 5 equivalents, specifically about 3 to 5 equivalents, with respect to the (R)-phthalimido-2-acetyloxypropyl-carbamate compound of formula III in order to ensure a proper course of the reaction.

In one embodiment, the reaction in step-(b) is carried out at a temperature of about 0° C. to the reflux temperature of the solvent used, specifically at a temperature of about 20° C. to the reflux temperature of the solvent used, and most specifically at the reflux temperature of the solvent used. The reaction time may vary between about 3 hours to about 10 hours, and specifically about 4 hours to about 6 hours.

The reaction mass containing the Linezolid of formula I obtained may be subjected to usual work up such as a washing, an extraction, an evaporation, a pH adjustment etc., followed by isolation and/or recrystallization from a suitable solvent by conventional methods such as cooling, seeding, partial removal of the solvent from the solution, by adding an anti-solvent to the solution, evaporation, vacuum distillation, or a combination thereof.

It has been found that two novel intermediate compounds, namely (R)-amino-2-acetyloxypropyl-carbamate compound of formula V and (R)-acetamido-2-hydroxypropyl-carbamate compound of formula XI, are formed when reacting the (R)-phthalimido-2-acetyloxypropyl-carbamate compound of formula III with the primary amine formation agent and these novel compounds may be isolated using the methods described herein. The novel compounds of formula V and formula XI are characterized by having the following structural formulae:

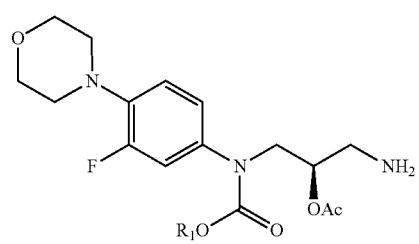

V

XI

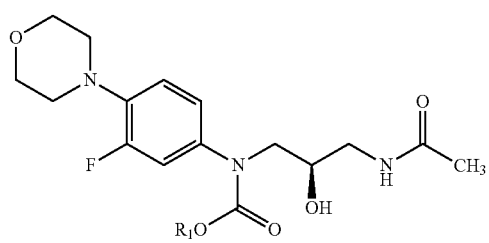

Particular variations of reaction conditions and parameters (e.g., temperature, time, reagent, base, solvent, etc.) may permit the isolation of the compounds of formulae V and XI. For example, use of mild reaction conditions (e.g. low temperatures and mild base) may permit isolation of the compound of formula V. Application of heat to the compound of formula V optionally in the presence of a base may permit the isolation of the compound of formula XI. In one embodiment, the reaction time may vary between about 30 minutes to about 10 hours and specifically about 1 hour to about 3 hours. The isolated novel intermediate compounds of formulae V and XI may be further converted into linezolid of formula I using the methods described herein.

The solvent used for washing, extracting, isolating and/or recrystallizing the pure Linezolid of formula I is selected from the group as described herein above. Specifically, the solvent is selected from the group consisting of water, methanol, ethanol, n-propanol, isopropyl alcohol, acetone, tetrahydrofuran, 2-methyl-tetrahydrofuran, diisopropyl ether, methyl tert-butyl ether, ethyl acetate, n-pentane, n-hexane, n-heptane, cyclohexane, toluene, xylene, dichloromethane, dichloroethane, chloroform, and mixtures thereof. Most specifically, the solvent is selected from the group consisting of water, methanol, ethanol, n-propanol, isopropyl alcohol, acetone, ethyl acetate, dichloromethane, and mixtures thereof.

In one embodiment, the isolation is carried out by cooling the reaction mass at a temperature of below about 35° C., followed by the addition of water at a temperature of about 10° C. to about 35° C., and more specifically at a temperature of about 20° C. to about 30° C. After completion of addition process, the resulting mass is optionally stirred at a temperature of about 10° C. to about 35° C. for at least 10 minutes, and most specifically at a temperature of about 20° C. to about 30° C. for about 15 minutes to about 2 hours.

In another embodiment, the isolation is carried out by cooling the reaction mass while stirring at a temperature below about 30° C. and more specifically at about 20° C. to about 30° C.

The solid obtained is collected by filtration, filtration under vacuum, decantation, centrifugation, filtration employing a filtration media of a silica gel or celite, or a combination thereof.

The novel (R)-phthalimido-2-hydroxypropyl-carbamate compound of formula IV employed as intermediate in the process for manufacture of Linezolid disclosed herein allows the product to be easily isolated and purified, thereby producing a product with 70-80% overall yield.

According to another aspect, there is provided a process for the preparation of Linezolid of formula I, or an enantiomeric form or a mixture of enantiomeric forms thereof, comprising reacting the (R)-phthalimido-2-acetyloxypropyl-carbamate compound of formula III:

III

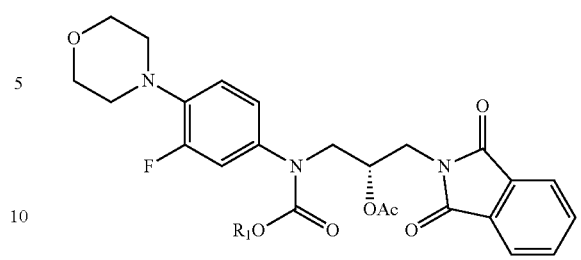

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group;
with a suitable reagent, optionally in the presence of a base, to produce the Linezolid of formula I.

In one embodiment, the radical $R_1$ in the compounds of formula III is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

The process for the preparation of linezolid of formula I disclosed herein is carried out by using the methods, reagents and Parameters as described hereinabove.

According to another aspect, there is provided a process for the preparation of (R)-phthalimido-2-acetyloxypropyl-carbamate compound of formula III:

III

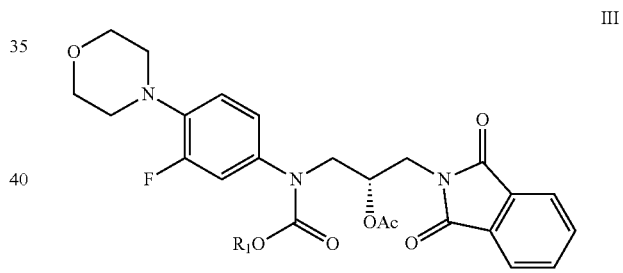

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group;
comprising acetylating (R)-phthalimido-2-hydroxypropyl-carbamate compound of formula IV:

IV

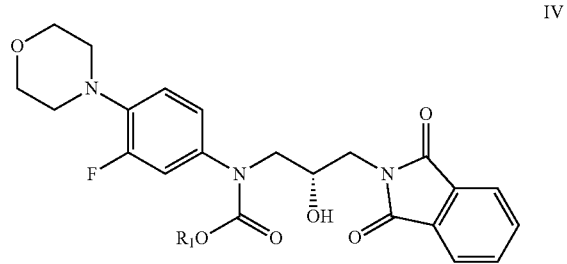

or an enantiomeric form or a mixture of enantiomeric forms thereof, wherein $R_1$ is as defined above; with an acetylating agent optionally in the presence of a base to produce an (R)-phthalimido-2-acetyloxypropyl-carbamate compound of formula III or an enantiomeric form or a mixture of enantiomeric forms thereof.

In one embodiment, the radical $R_1$ in the compounds of formulae III & IV is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

The process for the preparation of (R)-phthalimido-2-acetyloxypropyl-carbamate compound of formula III disclosed herein is carried out by using the methods, reagents and parameters as described hereinabove.

According to another aspect, there is provided an improved and cost effective process for the preparation of Linezolid of formula I, or an enantiomeric form or a mixture of enantiomeric forms thereof, which comprises:
a) reacting (R)-phthalimido-2-hydroxypropyl-carbamate compound of formula IV:

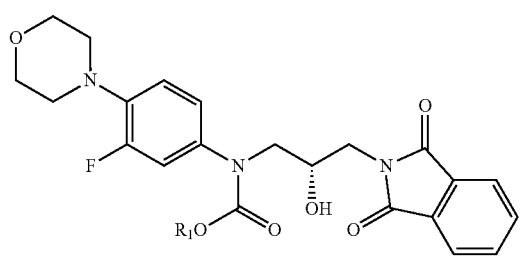

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; with a suitable reagent, optionally in the presence of a base, to produce (S)—N-[3-fluoro-4-(4-morpholinyl)phenyl]-2-oxo-5-oxazolidinyl-methyl amine of formula II:

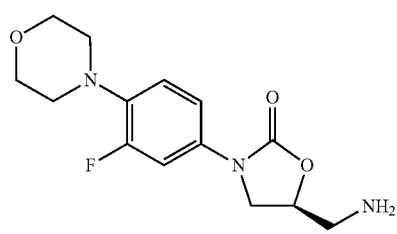

or an enantiomeric form or a mixture of enantiomeric forms thereof, or a salt thereof; and
b) acetylating the amine compound of formula II with a suitable acetylating agent to produce the Linezolid of formula I.

In one embodiment, the radical $R_1$ in the compounds of formula IV is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

The reagent used in step-(a) is a primary amine formation agent. Exemplary primary amine formation agents used in step-(a) include, but are not limited to, hydrazine hydrate, methyl amine, and the like. A most specific reagent is hydrazine hydrate or aqueous methyl amine.

In another embodiment, the reaction in step-(a) is carried out in the presence of a base. Specifically, the base is an organic or inorganic base, and most specifically an inorganic base, selected from the group as described hereinabove.

Specific bases are aqueous ammonia, sodium hydroxide, calcium hydroxide, magnesium hydroxide, potassium hydroxide, sodium carbonate, potassium carbonate, sodium bicarbonate, potassium bicarbonate, sodium tert-butoxide, sodium isopropoxide and potassium tert-butoxide; and most specifically potassium carbonate.

In one embodiment, the reaction in step-(a) is carried out in the presence of a solvent. Exemplary solvents used in step-(a) include, but are not limited to, water, an alcohol, a hydrocarbon solvent, an ester, a ketone, an ether, a nitrile, a polar aprotic solvent, a halogenated hydrocarbon solvent, and mixtures thereof.

Specifically, the solvent used in step-(a) is selected from the group consisting of water, methanol, ethanol, isopropanol, n-butanol, ethyl acetate, methyl acetate, isopropyl acetate, tert-butyl methyl acetate, ethyl formate, acetone, n-pentane, n-hexane, n-heptane, cyclohexane, toluene, xylene, tetrahydrofuran, 2-methyl-tetrahydrofuran, dioxane, diethyl ether, diisopropyl ether, methyl tert-butyl ether, mono glyme, diglyme, acetonitrile, propionitrile, N,N-dimethylformamide, N,N-dimethylacetamide, dimethylsulfoxide, dichloromethane, dichloroethane, and mixtures thereof. Most specifically, the solvent is selected from the group consisting of methanol, ethanol, isopropanol, acetone, and mixtures thereof.

In one embodiment, the reagent in step-(a) is used in a ratio of about 1 to 5 equivalents, specifically about 3 to 5 equivalents, with respect to the (R)-phthalimido-2-hydroxypropyl-carbamate compound of formula IV in order to ensure a proper course of the reaction.

In one embodiment, the reaction in step-(a) is carried out at a temperature of about 0° C. to the reflux temperature of the solvent used, specifically at a temperature of about 20° C. to the reflux temperature of the solvent used, and most specifically at the reflux temperature of the solvent used. The reaction time may vary between about 2 hours to about 8 hours, and specifically about 3 hours to about 4 hours. The reaction mass containing the (S)—N-[3-fluoro-4-(4-morpholinyl)phenyl]-2-oxo-5-oxazolidinyl-methyl amine of formula II obtained in step-(a) may be subjected to usual work up methods as described hereinabove. The reaction mass may be used directly in the next step to produce the Linezolid of formula I, or the compound of formula II may be isolated and/or recrystallized and then used in the next step.

In one embodiment, the (S)—N-[3-fluoro-4-(4-morpholinyl)phenyl]-2-oxo-5-oxazolidinyl-methyl amine of formula II is isolated and/or re-crystallized from a suitable solvent by the methods as described hereinabove.

It has been found that a novel intermediate compound, (R)-amino-2-hydroxypropyl-carbamate compound, of formula VI is formed when reacting the (R)-phthalimido-2-hydroxypropyl-carbamate compound of formula IV with the primary amine formation agent and it may be isolated using the methods described herein. The novel compound of formula VI is characterized by having the following structural formula:

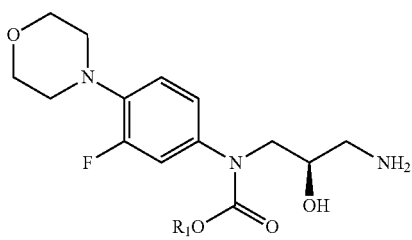

VI

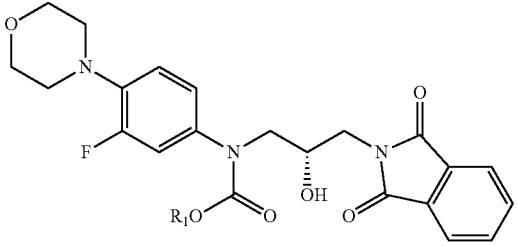

IV

Particular variations of reaction conditions and parameters (e.g., temperature, time, reagent, base, solvent, etc.) may permit the isolation of the compound of formula VI. For example, use of mild reaction conditions (e.g. low temperatures and mild base) may permit isolation of the compound of formula VI. The isolated novel intermediate compound of formulae VI may be further converted into linezolid of formula I using the methods described herein.

The solvent used for isolating and/or recrystallizing the (S)—N-[3-fluoro-4-(4-morpholinyl)phenyl]-2-oxo-5-oxazolidinyl-methyl amine of formula II is selected from the group as described above for such purpose. Specifically, the solvent is selected from the group consisting of water, methanol, ethanol, n-propanol, isopropyl alcohol, acetone, tetrahydrofuran, 2-methyl-tetrahydrofuran, diisopropyl ether, methyl tert-butyl ether, ethyl acetate, n-pentane, n-hexane, n-heptane, cyclohexane, toluene, xylene, dichloromethane, dichloroethane, chloroform, and mixtures thereof.

The acetylation reaction in step-(b) is carried out by the methods known in the art. Exemplary acetylating agents used in step-(b) include, but are not limited to, acetyl halide such as acetyl chloride, acetyl bromide, acetyl iodide; acetic anhydride, sodium acetate, and the like, or a combination thereof. A most specific acetylating agent is acetic anhydride.

The reaction mass containing the linezolid of formula I obtained in step-(b) may be subjected to usual work up, followed by isolation and/or recrystallization from a suitable solvent using the methods as described herein above.

According to another aspect, there is provided an improved process for the preparation of (S)—N-[3-fluoro-4-(4-morpholinyl)phenyl]-2-oxo-5-oxazolidinyl-methyl amine of formula II:

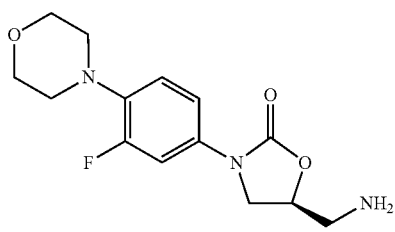

II or an enantiomeric form or a mixture of enantiomeric forms thereof, or a salt thereof;

comprising reacting (R)-phthalimido-2-hydroxypropyl-carbamate compound of formula IV:

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; with a suitable reagent, optionally in the presence of a base, to produce the aminomethyl compound of formula II, or an enantiomeric form or a mixture of enantiomeric forms thereof, or a salt thereof.

In one embodiment, the radical $R_1$ in the compounds of formulae IV is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

The process for the preparation of (S)—N-[3-fluoro-4-(4-morpholinyl)phenyl]-2-oxo-5-oxazolidinyl-methyl amine of formula II disclosed herein is carried out by using the methods, reagents and parameters as described hereinabove.

According to another aspect, there is provided a process for the preparation of (R)-phthalimido-2-hydroxypropyl-carbamate compound of formula IV:

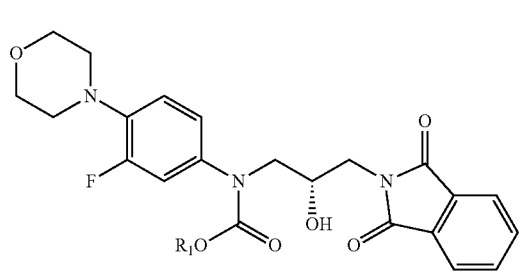

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; comprising reacting N-[3-phthalimido-2-(R)-hydroxypropyl]-3-fluoro-4-(4-morpholinyl)aniline of formula XIII:

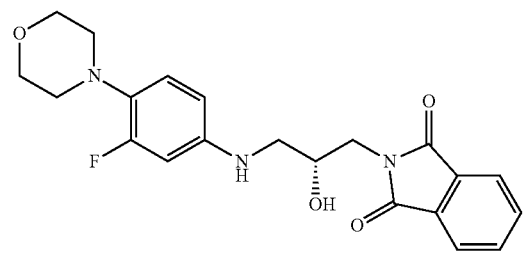

XIII or an enantiomeric form or a mixture of enantiomeric forms thereof, or a salt thereof;

with a suitable activating agent, optionally in the presence of a base, wherein the activating agent is a carbonate compound of formula XIVa, or a chloroformate compound of formula XIVb:

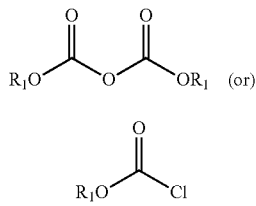

wherein the radical $R_1$ is as defined in Formula IV; to produce the (R)-phthalimido-2-hydroxypropyl-carbamate compound of formula IV or an enantiomeric form or a mixture of enantiomeric forms thereof.

In one embodiment, the radical $R_1$ in the compounds of formulae IV, XIVa & XIVb is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

Unless otherwise specified, the N-[3-phthalimido-2-(R)-hydroxypropyl]-3-fluoro-4-(4-morpholinyl)aniline of formula XIII as used herein as starting material is a known compound and can be obtained by the processes described in the prior art, for example, the processes described in the U.S. Pat. No. 7,429,661 B2 assigned to Symed Labs Limited (the present applicant).

In one embodiment, the reaction between the compounds of formula XIII and XIVa or XIVb is carried out in the presence of a base. Specifically, the base is an organic or inorganic base, and most specifically an organic base.

Exemplary bases include, but are not limited to, hydroxides, alkoxides, bicarbonates and carbonates of alkali or alkaline earth metals; ammonia, collidine, trimethylamine, tributylamine, triethylamine, diisopropylethylamine, N-methylmorpholine, and 1-alkylimidazole.

Specific bases are trimethylamine, tributylamine, triethylamine, diisopropylethylamine and N-methylmorpholine; and most specifically diisopropylethylamine.

In one embodiment, the reaction between the compounds of formula XIII and XIVa or XIVb is carried out in the presence of a solvent. Exemplary solvents used herein include, but are not limited to, water, an alcohol, a hydrocarbon solvent, an ester, a ketone, an ether, a nitrile, a polar aprotic solvent, a halogenated hydrocarbon solvent, and mixtures thereof. A most specific solvent is dichloromethane.

In one embodiment, the activating agent of formula XIVa or XIVb is used in a ratio of about 1 to 3 equivalents, specifically about 1.1 to 1.5 equivalents, with respect to the N-[3-phthalimido-2-(R)-hydroxypropyl]-3-fluoro-4-(4-morpholinyl)aniline of formula XIII in order to ensure a proper course of the reaction.

In one embodiment, the reaction between the compounds of formula XIII and the activating agent is carried out at a temperature of about 0° C. to the reflux temperature of the solvent used, specifically at a temperature of about 10° C. to the reflux temperature of the solvent used, and most specifically at a temperature of about 20° C. to about 40° C. The reaction time may vary between about 30 minutes to about 8 hours, specifically about 1 hour to about 5 hours, and more specifically about 1 hour to about 2 hours.

The reaction mass containing the (R)-phthalimido-2-hydroxypropyl-carbamate compound of formula IV obtained may be subjected to usual work up, followed by isolation and/or recrystallization from a suitable solvent using the methods as described herein above.

The solvent used for isolating and/or recrystallizing the (R)-phthalimido-2-hydroxypropyl-carbamate compound of formula IV is selected from the group as described herein above.

In one embodiment, a most specific (R)-phthalimido-2-hydroxypropyl-carbamate compound of formula IV prepared by the process described herein is N-[3-phthalimido-2-(R)-hydroxypropyl]-N-[3-fluoro-4-(4-morpholinyl)phenyl]-carbamic acid ethyl ester of formula IVa (formula IV, wherein $R_1$ is ethyl):

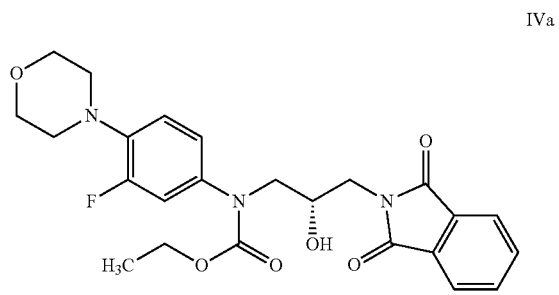 [SMILES: CCOC(=O)N(C[C@@H](O)CN1C(=O)c2ccccc2C1=O)c1ccc(N2CCOCC2)c(F)c1]

or an enantiomeric form or a mixture of enantiomeric forms thereof.

In another embodiment, a most specific (R)-phthalimido-2-hydroxypropyl-carbamate compound of formula IV prepared by the process described herein is N-[3-phthalimido-2-(R)-hydroxypropyl]-N-[3-fluoro-4-(4-morpholinyl)phenyl]-carbamic acid tert-butyl ester of formula IVb (formula IV, wherein $R_1$ is tert-butyl):

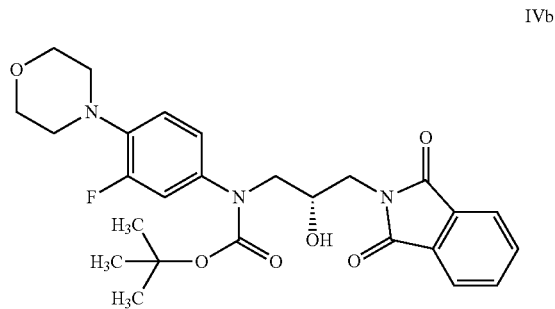 [SMILES: CC(C)(C)OC(=O)N(C[C@@H](O)CN1C(=O)c2ccccc2C1=O)c1ccc(N2CCOCC2)c(F)c1]

or an enantiomeric form or a mixture of enantiomeric forms thereof.

In another embodiment, a most specific (R)-phthalimido-2-hydroxypropyl-carbamate compound of formula IV prepared by the process described, herein is N-[3-phthalimido-2-(R)-hydroxypropyl]-N-[3-fluoro-4-(4-morpholinyl)phenyl]-carbamic acid benzyl ester of formula IVc (formula IV, wherein $R_1$ is benzyl):

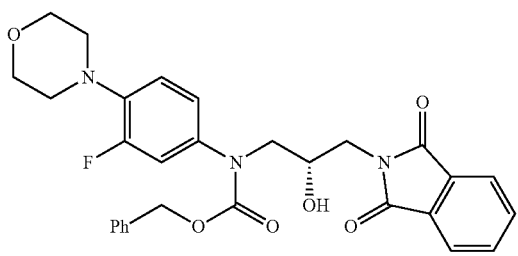

or an enantiomeric form or a mixture of enantiomeric forms thereof.

According to another aspect, there is provided a process for the preparation of (R)-phthalimido-2-hydroxypropyl-carbamate compound of formula IV:

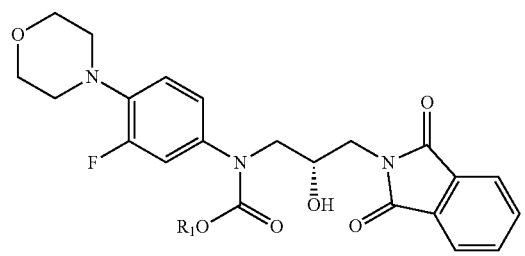

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; which comprises:

a) reacting a (R)-2-hydroxypropyl-aniline compound of formula XV or N-[2(R)-2,3-epoxypropyl]-3-fluoro-4-(4-morpholinyl)aniline of formula X:

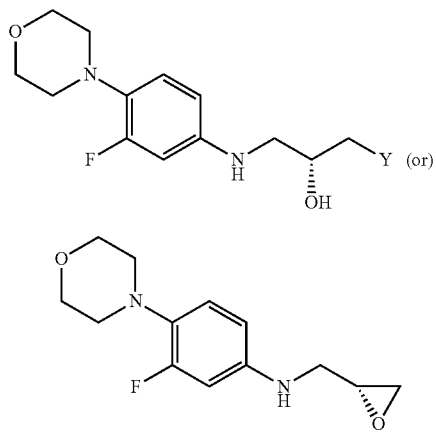

or an enantiomeric form or a mixture of enantiomeric forms thereof, or a salt thereof, wherein Y is a leaving group such as a halogen or a sulfonyloxy group; with a suitable activating agent, optionally in the presence of a base, wherein the activating agent is a carbonate compound of formula XIVa, or a chloroformate compound of formula XIVb:

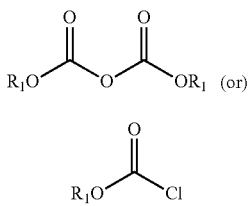

wherein the radical $R_1$ is as defined in Formula IV; to produce an (R)-2-hydroxypropyl-carbamate compound of formula VII or an (R)-2,3-epoxypropyl-carbamate compound of formula IX:

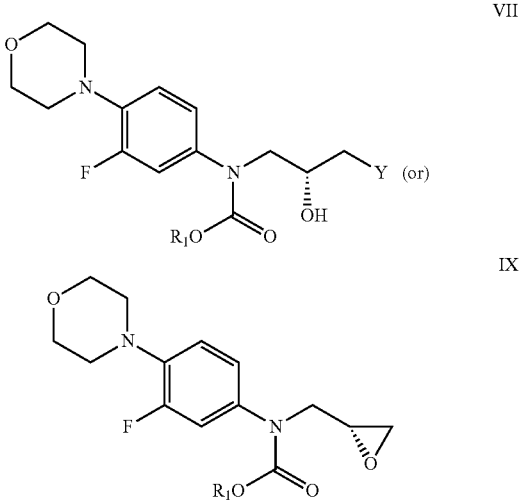

or an enantiomeric form or a mixture of enantiomeric forms thereof, wherein $R_1$ and Y are as defined above; and b) reacting the (R)-2-hydroxypropyl-carbamate compound of formula VII or the (R)-2,3-epoxypropyl-carbamate compound of formula IX obtained in step-(a) with potassium phthalimide, optionally in the presence of a base, to produce the (R)-phthalimido-2-hydroxypropyl-carbamate compound of formula IV or an enantiomeric form or a mixture of enantiomeric forms thereof.

In one embodiment, the radical $R_1$ in the compounds of formulae IV, VII, IX, XIVa & XIVb is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

In another embodiment, the leaving group Y in the compounds of formulae VII and XV is a halogen, or an alkyl or aryl sulfonyloxy group. Specifically, the leaving group Y is selected from the group consisting of Cl, Br, I, methanesulfonyloxy, toluenesulfonyloxy and trifluoromethanesulfonyloxy group; more specifically the leaving group Y is Cl or toluenesulfonyloxy; and a most specific leaving group is Cl.

The compounds of formulae IV, VII, IX & X disclosed herein are novel and constitute another aspect of the present invention.

The use of the novel intermediate compounds of formulae IV, VII, IX & X in the preparation of Linezolid of formula I is novel and forms further aspect of the present invention.

Unless otherwise specified, the (R)-2-hydroxypropyl-aniline compound of formula XV as used herein as starting material is a known compound and can be obtained by the processes described in the prior art, for example, the processes described in the U.S. Pat. No. 7,307,163 B2 assigned to Symed Labs Limited (the present applicant).

In one embodiment, the reaction in step-(a) is carried out in the presence of a base. Specifically, the base is an organic or inorganic base, and most specifically an organic base, selected from the group as described herein above.

Exemplary bases include, but are not limited to, hydroxides, alkoxides, bicarbonates and carbonates of alkali or alkaline earth metals; ammonia, collidine, trimethylamine, tributylamine, triethylamine, diisopropylethylamine, N-methylmorpholine, and 1-alkylimidazole.

Specific bases are trimethylamine, tributylamine, triethylamine, diisopropylethylamine and N-methylmorpholine; and most specifically diisopropylethylamine.

In one embodiment, the reaction in step-(a) is carried out in the presence of a solvent. Exemplary solvents used herein include, but are not limited to, water, an alcohol, a hydrocarbon solvent, an ester, a ketone, an ether, a nitrile, a polar aprotic solvent, a halogenated hydrocarbon solvent, and mixtures thereof. A most specific solvent is dichloromethane.

In one embodiment, the activating agent of formula XIVa or XIVb is used in a ratio of about 1 to 3 equivalents, specifically about 1.1 to 1.5 equivalents, with respect to the (R)-2-hydroxypropyl-aniline compound of formula XV, or N-[2(R)-2,3-epoxypropyl]-3-fluoro-4-(4-morpholinyl)aniline of formula X, in order to ensure a proper course of the reaction.

In one embodiment, the reaction in step-(a) is carried out at a temperature of about 0° C. to the reflux temperature of the solvent used, specifically at a temperature of about 10° C. to the reflux temperature of the solvent used, and most specifically at a temperature of about 20° C. to about 40° C. The reaction time may vary between about 30 minutes to about 8 hours, specifically about 1 hour to about 5 hours, and more specifically about 1 hour to about 2 hours.

The reaction mass containing the (R)-2-hydroxypropyl-carbamate compound of formula VII or an (R)-2,3-epoxypropyl-carbamate compound of formula IX obtained in step-(a) may be subjected to usual work up such as a washing, an extraction, a pH adjustment, an evaporation, a layer separation, a decolorization, or a combination thereof. The reaction mass may be used directly in the next step to produce the (R)-phthalimido-2-hydroxypropyl-carbamate compound of formula IV, or the compound of formula VII or IX may be isolated and/or recrystallized and then used in the next step.

In one embodiment, the (R)-2-hydroxypropyl-carbamate compound of formula VII or an (R)-2,3-epoxypropyl-carbamate compound of formula IX is isolated and/or recrystallized from a suitable solvent by conventional methods such as cooling, seeding, partial removal of the solvent from the solution, by adding an anti-solvent to the solution, evaporation, vacuum distillation, or a combination thereof.

The solvent used for isolating and/or recrystallizing the (R)-2-hydroxypropyl-carbamate compound of formula VII or an (R)-2,3-epoxypropyl-carbamate compound of formula IX is selected from the group as described herein above.

In another embodiment, the reaction in step-(b) is optionally carried out in the presence of a base. Specifically, the base is an organic or inorganic base selected from the group as described hereinabove.

In one embodiment, the reaction in step-(b) is carried out in the presence of a solvent. Exemplary solvents used in step-(b) include, but are not limited to, water, an alcohol, a hydrocarbon solvent, an ester, a ketone, an ether, a nitrile, a polar aprotic solvent, a halogenated hydrocarbon solvent, and mixtures thereof.

Specifically, the solvent used in step-(b) is selected from the group acetonitrile, propionitrile, N,N-dimethylformamide, N,N-dimethylacetamide, dimethylsulfoxide, dichloromethane, dichloroethane, and mixtures thereof. Most specific solvents are acetonitrile, N,N-dimethylformamide, and mixtures thereof.

In one embodiment, the potassium phthalimide in step-(b) is used in a ratio of about 1 to 2 equivalents, specifically about 1.1 to 1.5 equivalents, with respect to the (R)-2-hydroxypropyl-carbamate compound of formula VII or the (R)-2,3-epoxypropyl-carbamate compound of formula IX in order to ensure a proper course of the reaction.

In one embodiment, the reaction in step-(b) is carried out at a temperature of about 0° C. to the reflux temperature of the solvent used, specifically at a temperature of about 20° C. to the reflux temperature of the solvent used, and most specifically at the reflux temperature of the solvent used. The reaction time may vary between about 1 hour to about 10 hours, and specifically about 4 hours to about 6 hours.

The reaction mass containing the (R)-phthalimido-2-hydroxypropyl-carbamate compound of formula IV obtained may be subjected to usual work up, followed by isolation and/or recrystallization from a suitable solvent by the methods as described herein above.

The solvent used for washing, extracting, isolating and/or recrystallizing the (R)-phthalimido-2-hydroxypropyl-carbamate compound of formula IV is selected from the group as described herein above.

The solid obtained in step-(b) is collected by filtration, filtration under vacuum, decantation, centrifugation, filtration employing a filtration media of a silica gel or celite, or a combination thereof.

In one embodiment, a most specific (R)-2-hydroxypropyl-carbamate compound of formula VII prepared by the process described herein is N-[3-Chloro-2-(R)-hydroxypropyl]-N-[3-fluoro-4-(4-morpholinyl)phenyl]-carbamic acid ethyl ester of formula VIIa (formula VII, wherein $R_1$ is ethyl and Y is Cl):

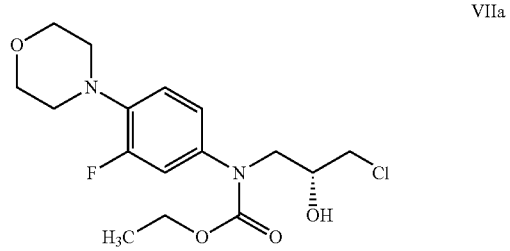 [SMILES: CCOC(=O)N(C[C@@H](O)CCl)c1ccc(N2CCOCC2)c(F)c1]

VIIa or an enantiomeric form or a mixture of enantiomeric forms thereof.

In another embodiment, a most specific (R)-2,3-epoxypropyl-carbamate compound of formula IX prepared by the process described herein is N-[2(R)-2,3-epoxypropyl]-N-[3-fluoro-4-(4-morpholinyl)phenyl]-carbamic acid ethyl ester of formula IXa (formula IX, wherein $R_1$ is ethyl):

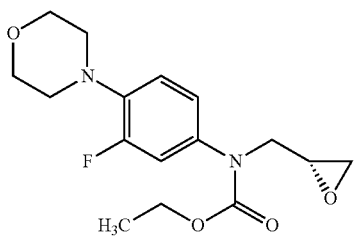

IXa or an enantiomeric form or a mixture of enantiomeric forms thereof.

According to another aspect, there is provided a process for the preparation of (R)-phthalimido-2-hydroxypropyl-carbamate compound of formula IV:

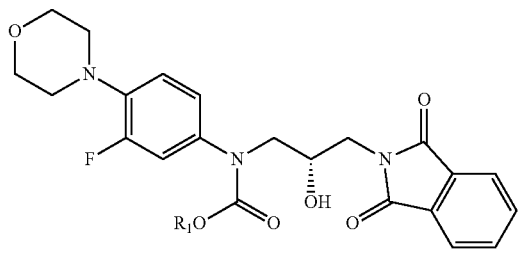

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; comprising reacting the (R)-2-hydroxypropyl-carbamate compound of formula VII or the (R)-2,3-epoxypropyl-carbamate compound of formula IX:

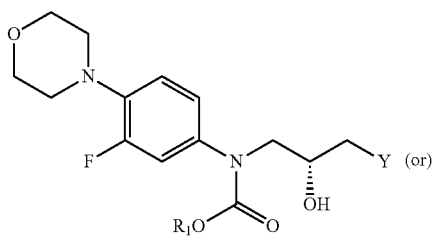

VII

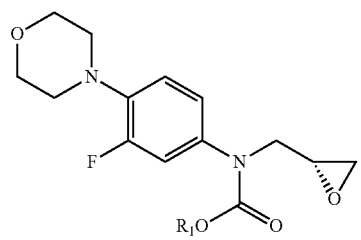

IX or an enantiomeric form or a mixture of enantiomeric forms thereof, wherein $R_1$ is as defined in Formula IV, and Y is a leaving group such as a halogen or a sulfonyloxy group; with potassium phthalimide, optionally in the presence of a base, to produce the (R)-phthalimido-2-hydroxypropyl-carbamate compound of formula IV or an enantiomeric form or a mixture of enantiomeric forms thereof.

In one embodiment, the radical $R_1$ in the compounds of formulae IV, VII & IX is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

In one embodiment, the leaving group Y in the compound of formula VII is a halogen, or an alkyl or aryl sulfonyloxy group. Specifically, the leaving group Y is selected from the group consisting of Cl, Br, I, methanesulfonyloxy, toluenesulfonyloxy and trifluoromethanesulfonyloxy group; more specifically the leaving group Y is Cl or toluenesulfonyloxy; and a most specific leaving group is Cl.

The process for the preparation of (R)-phthalimido-2-hydroxypropyl-carbamate compound of formula IV disclosed herein is carried out by using the methods, reagents and parameters as described hereinabove.

According to another aspect, there is provided a process for the preparation of (R)-2-hydroxypropyl-carbamate compound of formula VII or the (R)-2,3-epoxypropyl-carbamate compound of formula IX:

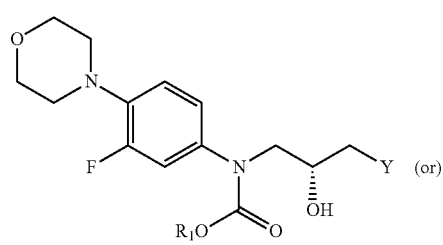

VII

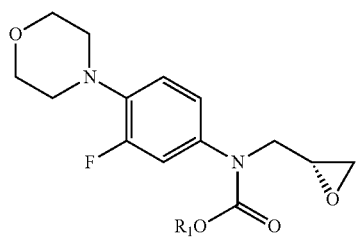

IX or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl, and Y is a leaving group such as a halogen or a sulfonyloxy group; comprising reacting a (R)-2-hydroxypropyl-aniline compound of formula XV or N-[2(R)-2,3-epoxypropyl]-3-fluoro-4-(4-morpholinyl)aniline of formula X:

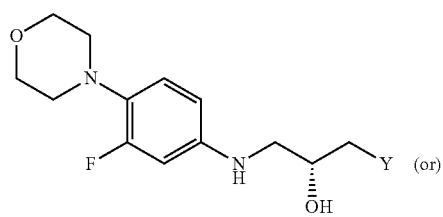

XV

-continued

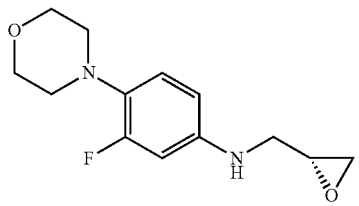

X or an enantiomeric form or a mixture of enantiomeric forms thereof, or a salt thereof, wherein Y is a leaving group such as a halogen or a sulfonyloxy group;

with a suitable activating agent, optionally in the presence of a base, wherein the activating agent is a carbonate compound of formula XIVa, or a chloroformate compound of formula XIVb:

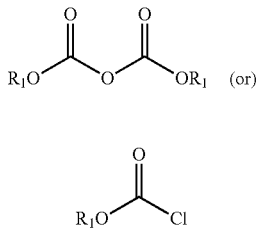

XIVa

XIVb wherein the radical $R_1$ is as defined above; to produce the (R)-2-hydroxypropyl-carbamate compound of formula VII or the (R)-2,3-epoxypropyl-carbamate compound of formula IX or an enantiomeric form or a mixture of enantiomeric forms thereof.

In one embodiment, the radical $R_1$ in the compounds of formulae VII, IX, XIVa & XIVb is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

In one embodiment, the leaving group Y in the compound of formula VII & XV is a halogen, or an alkyl or aryl sulfonyloxy group. Specifically, the leaving group Y is selected from the group consisting of Cl, Br, I, methanesulfonyloxy, toluenesulfonyloxy and trifluoromethanesulfonyloxy group; more specifically the leaving group Y is Cl or toluenesulfonyloxy; and a most specific leaving group is Cl.

The process for the preparation of (R)-2-hydroxypropyl-carbamate compound of formula VII or the (R)-2,3-epoxypropyl-carbamate compound of formula IX disclosed herein is carried out by using the methods, reagents and parameters as described hereinabove.

According to another aspect, there is provided a process for the preparation of (R)-phthalimido-2-hydroxypropyl-carbamate compound of formula IV:

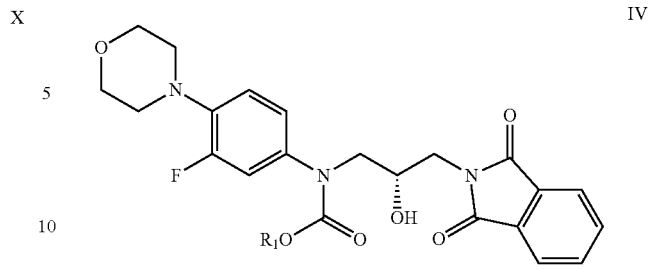

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; which comprises:

a) reacting a (R)-2-hydroxypropyl-aniline compound of formula XV or N-[2(R)-2,3-epoxypropyl]-3-fluoro-4-(4-morpholinyl)aniline of formula X:

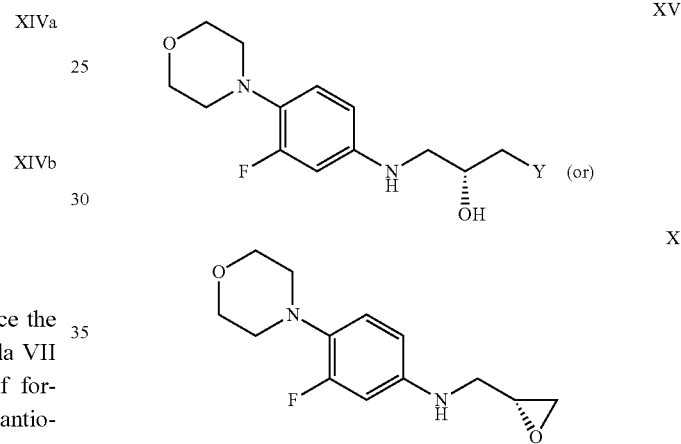

XV

X or an enantiomeric form or a mixture of enantiomeric forms thereof, or a salt thereof, wherein Y is a leaving group such as a halogen or a sulfonyloxy group;

with potassium phthalimide, optionally in the presence of a base, to produce N-[3-phthalimido-2-(R)-hydroxypropyl]-3-fluoro-4-(4-morpholinyl)aniline of formula XIII:

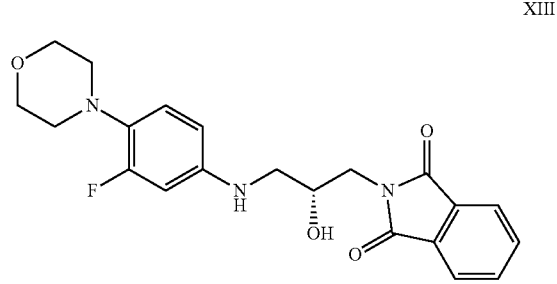 [SMILES: O=C1c2ccccc2C(=O)N1C[C@H](O)CNc1ccc(N2CCOCC2)c(F)c1]

XIII or an enantiomeric form or a mixture of enantiomeric forms thereof, or a salt thereof; and b) reacting the N-[3-phthalimido-2-(R)-hydroxypropyl]-3-fluoro-4-(4-morpholinyl)aniline of formula XIII or an enantiomeric form or a mixture of enantiomeric forms thereof, or a salt thereof; with a suitable activating agent, optionally in the presence of a base, wherein the activating agent is a carbonate compound of formula XIVa, or a chloroformate compound of formula XIVb:

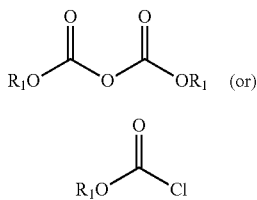

wherein the radical $R_1$ is as defined in Formula IV; to produce the (R)-phthalimido-2-hydroxypropyl-carbamate compound of formula IV or an enantiomeric form or a mixture of enantiomeric forms thereof.

In one embodiment, the radical $R_1$ in the compounds of formulae IV, XIVa & XIVb is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

In one embodiment, the leaving group Y in the compound of formula XV is a halogen, or an alkyl or aryl sulfonyloxy group. Specifically, the leaving group Y is selected from the group consisting of Cl, Br, I, methanesulfonyloxy, toluenesulfonyloxy and trifluoromethanesulfonyloxy group; more specifically the leaving group Y is Cl or toluenesulfonyloxy; and a most specific leaving group is Cl.

In another embodiment, the reaction in step-(a) is optionally carried out in the presence of a base. Specifically, the base is an organic or inorganic base selected from the group as described hereinabove.

In one embodiment, the reaction in step-(a) is carried out in the presence of a solvent. Exemplary solvents used in step-(a) include, but are not limited to, water, an alcohol, a hydrocarbon solvent, an ester, a ketone, an ether, a nitrile, a polar aprotic solvent, a halogenated hydrocarbon solvent, and mixtures thereof.

Specifically, the solvent used in step-(a) is selected from the group acetonitrile, propionitrile, N,N-dimethylformamide, N,N-dimethylacetamide, dimethylsulfoxide, dichloromethane, dichloroethane, and mixtures thereof. Most specific solvents are acetonitrile, N,N-dimethylformamide, and mixtures thereof.

In one embodiment, the potassium phthalimide in step-(a) is used in a ratio of about 1 to 2 equivalents, specifically about 1.1 to 1.5 equivalents, with respect to (R)-2-hydroxypropyl-aniline compound of formula XV or N-[2(R)-2,3-epoxypropyl]-3-fluoro-4-(4-morpholinyl)aniline of formula X in order to ensure a proper course of the reaction.

In one embodiment, the reaction in step-(a) is carried out at a temperature of about 0° C. to the reflux temperature of the solvent used, specifically at a temperature of about 20° C. to the reflux temperature of the solvent used, and most specifically at the reflux temperature of the solvent used. The reaction time may vary between about 1 hour to about 10 hours, and specifically about 3 hours to about 6 hours.

The reaction mass containing the N-[3-phthalimido-2-(R)-hydroxypropyl]-3-fluoro-4-(4-morpholinyl)aniline of formula XIII obtained in step-(a) may be subjected to usual work up such as a washing, an extraction, a pH adjustment, an evaporation, a layer separation, a decolorization, or a combination thereof. The reaction mass may be used directly in the next step to produce the (R)-phthalimido-2-hydroxypropyl-carbamate compound of formula IV, or the compound of formula XIII may be isolated and/or recrystallized and then used in the next step.

In one embodiment, the N-[3-phthalimido-2-(R)-hydroxypropyl]-3-fluoro-4-(4-morpholinyl)aniline of formula XIII is isolated and/or re-crystallized from a suitable solvent by the methods described herein above.

The solvent used for isolating and/or recrystallizing the N-[3-phthalimido-2-(R)-hydroxypropyl]-3-fluoro-4-(4-morpholinyl)aniline of formula XIII is selected from the group as described herein above.

In one embodiment, the reaction in step-(b) is carried out in the presence of a base. Specifically, the base is an organic or inorganic base, and most specifically an organic base, selected from the group as described herein above.

Specific bases are trimethylamine, tributylamine, triethylamine, diisopropylethylamine and N-methylmorpholine; and most specifically diisopropylethylamine.

In one embodiment, the reaction in step-(b) is carried out in the presence of a solvent. Exemplary solvents used herein include, but are not limited to, water, an alcohol, a hydrocarbon solvent, an ester, a ketone, an ether, a nitrile, a polar aprotic solvent, a halogenated hydrocarbon solvent, and mixtures thereof. A most specific solvent is dichloromethane.

In one embodiment, the activating agent of formula XIVa or XIVb is used in a ratio of about 1 to 3 equivalents, specifically about 1.1 to 1.5 equivalents, with respect to the N-[3-phthalimido-2-(R)-hydroxypropyl]-3-fluoro-4-(4-morpholinyl)aniline of formula XIII in order to ensure a proper course of the reaction.

In one embodiment, the reaction in step-(b) is carried out at a temperature of about 0° C. to the reflux temperature of the solvent used, specifically at a temperature of about 10° C. to the reflux temperature of the solvent used, and most specifically at a temperature of about 20° C. to about 40° C. The reaction time may vary between about 30 minutes to about 8 hours, specifically about 1 hour to about 5 hours, and more specifically about 1 hour to about 2 hours.

The reaction mass containing the (R)-phthalimido-2-hydroxypropyl-carbamate compound of formula IV obtained may be subjected to usual work up, followed by isolation and/or recrystallization from a suitable solvent by the methods as described herein above.

According to another aspect, there is provided a process for the preparation of N-[3-phthalimido-2-(R)-hydroxypropyl]-3-fluoro-4-(4-morpholinyl)aniline of formula XIII:

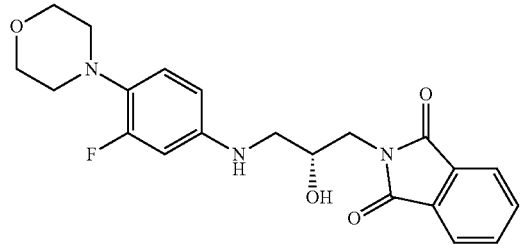

or an enantiomeric form or a mixture of enantiomeric forms thereof, or a salt thereof;
comprising reacting N-[2(R)-2,3-epoxypropyl]-3-fluoro-4-(4-morpholinyl)aniline of formula X:

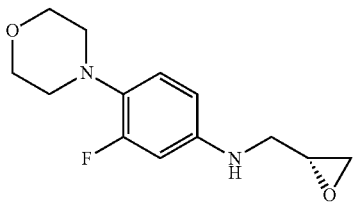

or an enantiomeric form or a mixture of enantiomeric forms thereof, or a salt thereof, with potassium phthalimide, optionally in the presence of a base, to produce N-[3-phthalimido-2-(R)-hydroxypropyl]-3-fluoro-4-(4-morpholinyl)aniline of formula XIII or an enantiomeric form or a mixture of enantiomeric forms thereof, or a salt thereof.

The process for the preparation of N-[3-phthalimido-2-(R)-hydroxypropyl]-3-fluoro-4-(4-morpholinyl)aniline of formula XIII disclosed herein is carried out by using the methods, reagents and parameters as described hereinabove.

According to another aspect, there is provided a process for the preparation of N-[2(R)-2,3-epoxypropyl]-3-fluoro-4-(4-morpholinyl)aniline of formula X:

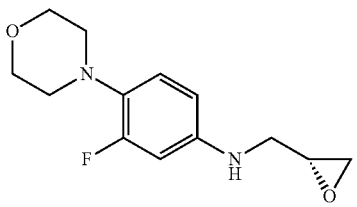

or an enantiomeric form or a mixture of enantiomeric forms thereof, or a salt thereof;
comprising reacting (R)-2-hydroxypropyl-aniline compound of formula XV:

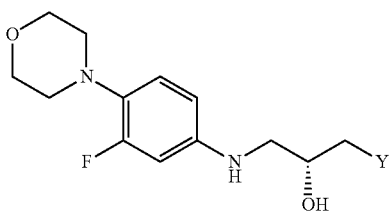

or an enantiomeric form or a mixture of enantiomeric forms thereof, or a salt thereof, wherein Y is a leaving group such as a halogen or a sulfonyloxy group; with a base to produce the N-[2(R)-2,3-epoxypropyl]-3-fluoro-4-(4-morpholinyl) aniline of formula X or an enantiomeric form or a mixture of enantiomeric forms thereof, or a salt thereof.

In one embodiment, the leaving group Y in the compound of formula XV is a halogen, or an alkyl or aryl sulfonyloxy group. Specifically, the leaving group Y is selected from the group consisting of Cl, Br, I, methanesulfonyloxy, toluenesulfonyloxy and trifluoromethanesulfonyloxy group; more specifically the leaving group Y is Cl or toluenesulfonyloxy; and a most specific leaving group is Cl.

In one embodiment, the base is an organic or inorganic base, and most specifically an inorganic base.

Exemplary bases include, but are not limited to, hydroxides, alkoxides, bicarbonates and carbonates of alkali or alkaline earth metals; ammonia, collidine, trimethylamine, tributylamine, triethylamine, diisopropylethylamine, N-methylmorpholine, and 1-alkylimidazole.

Specific bases are aqueous ammonia, potassium phosphate, sodium hydroxide, calcium hydroxide, magnesium hydroxide, potassium hydroxide, sodium carbonate, potassium carbonate, sodium bicarbonate, potassium bicarbonate, sodium tert-butoxide, sodium isopropoxide, potassium tert-butoxide, or a combination thereof; and most specifically potassium carbonate, sodium hydroxide and potassium hydroxide.

In one embodiment, the reaction between the (R)-2-hydroxypropyl-aniline compound of formula XV and the base is carried out in the presence of a solvent.

Exemplary solvents used herein include, but are not limited to, water, an alcohol, a hydrocarbon solvent, an ester, a ketone, an ether, a nitrile, a polar aprotic solvent, a halogenated hydrocarbon solvent, and mixtures thereof.

Specifically, the solvent is selected from the group consisting of water, methanol, ethanol, isopropanol, n-butanol, ethyl acetate, methyl acetate, isopropyl acetate, tert-butyl methyl acetate, ethyl formate, acetone, n-pentane, n-hexane, n-heptane, cyclohexane, toluene, xylene, tetrahydrofuran, 2-methyl-tetrahydrofuran, dioxane, diethyl ether, diisopropyl ether, methyl tert-butyl ether, monoglyme, diglyme, acetonitrile, propionitrile, N,N-dimethylformamide, N,N-dimethylacetamide, dimethylsulfoxide, dichloromethane, dichloroethane, and mixtures thereof. Most specific solvents are water, dichloromethane, and mixture thereof.

In one embodiment, the reaction between the (R)-2-hydroxypropyl-aniline compound of formula XV and the base is carried out at a temperature of about 0° C. to the reflux temperature of the solvent used, specifically at a temperature of about 10° C. to the reflux temperature of the solvent used, and most specifically at a temperature of about 20° C. to about 40° C. The reaction time may vary between about 1 to about 16 hours, specifically about 6 hour to about 15 hours, and more specifically about 12 hours to about 14 hours.

The reaction mass containing the of N-[2(R)-2,3-epoxypropyl]-3-fluoro-4-(4-morpholinyl)aniline of formula X obtained may be subjected to usual work up, followed by isolation and/or recrystallization from a suitable solvent using the methods as described herein above.

The solids obtained in any of the above process steps described hereinabove may be collected by filtration, filtration under vacuum, decantation, centrifugation, filtration employing a filtration media of a silica gel or celite, or a combination thereof.

Aptly the processes of the invention are adapted to the preparation of oxazolidinone derivatives, preferably Linezolid, in high enantiomeric and chemical purity.

The novel intermediate compounds of formulae III, IV, V, VI, VII, VIII, IX, X, XI and XII employed for the preparation of linezolid disclosed herein allows the product to be easily isolated and purified, thereby producing a product with 60-80% overall yield.

The highly pure linezolid obtained by the above processes may be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 35° C. to about 90° C., and specifically at about 75° C. to about 85° C. The drying can be carried out for any desired time period that achieves the desired result, such as times about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer, and the like.

In another embodiment, the highly pure linezolid obtained by the processes disclosed herein has a total purity, includes both chemical and enantiomeric purity, of greater than about 99%, specifically greater than about 99.5%, more specifically greater than about 99.9%, and most specifically greater than about 99.95% as measured by HPLC.

According to another aspect, there is provided a novel (R)-phthalimido-2-acetyloxypropyl-carbamate compound of formula III:

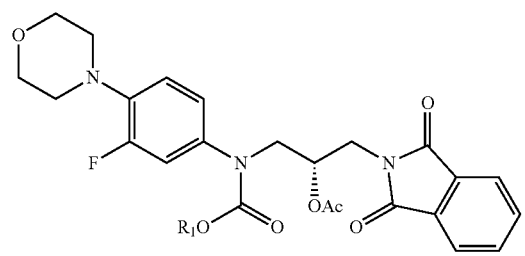

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

In one embodiment, a most specific (R)-phthalimido-2-acetyloxypropyl-carbamate compound of formula III disclosed herein is N-[3-phthalimido-2-(R)-acetyloxypropyl]-N-[3-fluoro-4-(4-morpholinyl)phenyl]-carbamic acid ethyl ester of formula IIIc (formula III, wherein $R_1$ is ethyl):

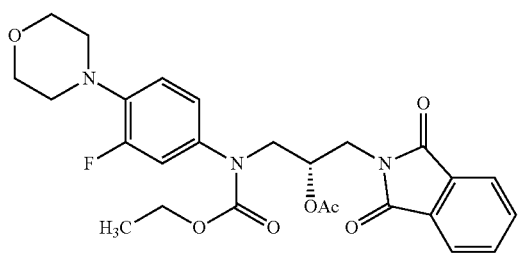

or an enantiomeric form or a mixture of enantiomeric forms thereof.

In another embodiment, a most specific (R)-phthalimido-2-acetyloxypropyl-carbamate compound of formula III disclosed herein is N-[3-phthalimido-2-(R)-acetyloxypropyl]-N-[3-fluoro-4-(4-morpholinyl)phenyl]-carbamic acid tert-butyl ester of formula IIIb (formula III, wherein $R_1$ is tert-butyl):

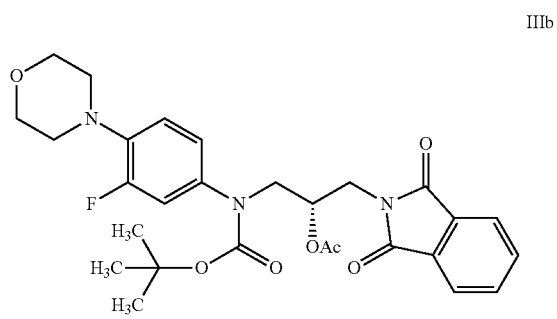

or an enantiomeric form or a mixture of enantiomeric forms thereof.

In another embodiment, a most specific (R)-phthalimido-2-acetyloxypropyl-carbamate compound of formula III disclosed herein is N-[3-phthalimido-2-(R)-acetyloxypropyl] N-[3-fluoro-4-(4-morpholinyl)phenyl]-carbamic acid benzyl ester of formula IIIc (formula III, wherein $R_1$ is benzyl):

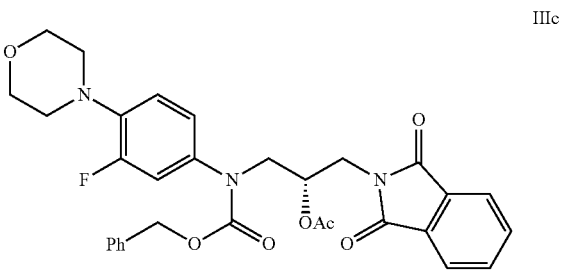 [SMILES: CC(=O)O[C@@H](CN1C(=O)c2ccccc2C1=O)CN(C(=O)OCc1ccccc1)c1ccc(N2CCOCC2)c(F)c1]

or an enantiomeric form or a mixture of enantiomeric forms thereof.

According to another aspect, there is provided a novel (R)-phthalimido-2-hydroxypropyl-carbamate compound of formula IV:

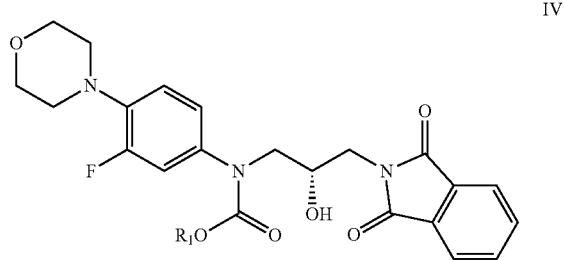

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl.

In one embodiment, a most specific (R)-phthalimido-2-hydroxypropyl-carbamate compound of formula IV disclosed herein is N-[3-phthalimido-2-(R)-hydroxypropyl]-N-[3-fluoro-4-(4-morpholinyl)phenyl]-carbamic acid ethyl ester of formula IVa (formula IV, wherein $R_1$ is ethyl):

IVa

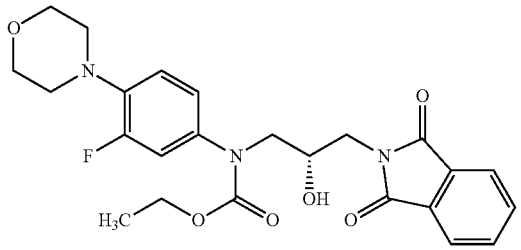

or an enantiomeric form or a mixture of enantiomeric forms thereof.

In another embodiment, a most specific (R)-phthalimido-2-hydroxypropyl-carbamate compound of formula IV disclosed herein is N-[3-phthalimido-2-(R)-hydroxypropyl]-N-[3-fluoro-4-(4-morpholinyl)phenyl]-carbamic acid tert-butyl ester of formula IVb (formula IV, wherein $R_1$ is tert-butyl):

IVb

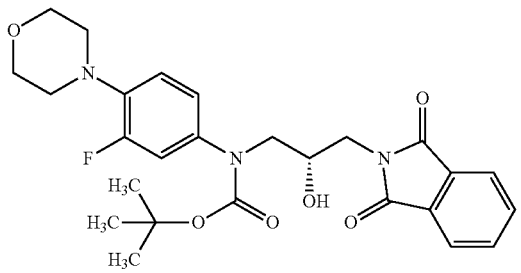

or an enantiomeric form or a mixture of enantiomeric forms thereof.

In another embodiment, a most specific (R)-phthalimido-2-hydroxypropyl-carbamate compound of formula IV disclosed herein is N-[3-phthalimido-2-(R)-hydroxypropyl]-N-[3-fluoro-4-(4-morpholinyl)phenyl]-carbamic acid benzyl ester of formula IVc (formula IV, wherein $R_1$ is benzyl):

IVc

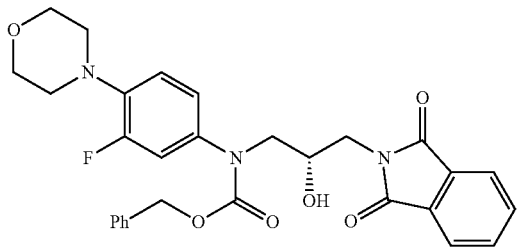

or an enantiomeric form or a mixture of enantiomeric forms thereof.

According to another aspect, there is provided a novel (R)-amino-2-acetyloxypropyl-carbamate compound of formula V:

V

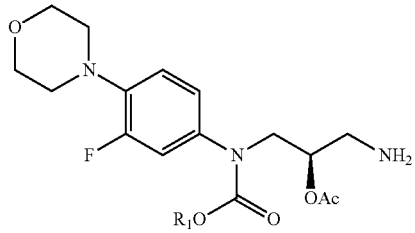

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

According to another aspect, there is provided a novel (R)-amino-2-hydroxypropyl-carbamate compound of formula VI:

VI

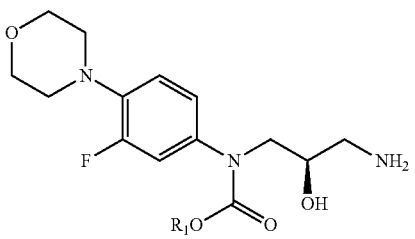

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl, According to another aspect, there is provided a novel (R)-2-hydroxypropyl-carbamate compound of formula VII:

VII

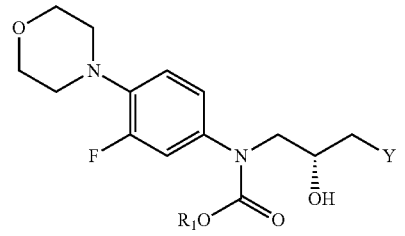

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and Y is a leaving group such as a halogen or a sulfonyloxy group.

According to another aspect, there is provided a novel (R)-2-acetyloxypropyl-carbamate compound of formula VIII:

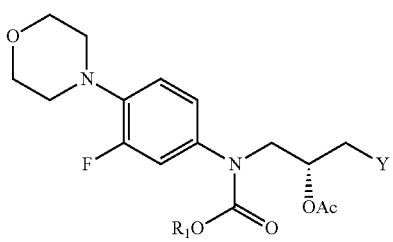

VIII or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; Y is a leaving group such as a halogen or a sulfonyloxy group, and 'Ac' represents an acetyl group.

According to another aspect, there is provided a novel (R)-2,3-epoxypropyl-carbamate compound of formula IX:

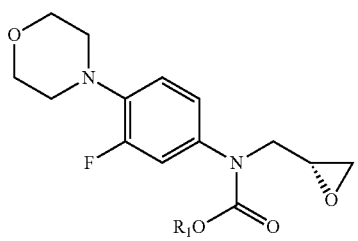

IX or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl.

According to another aspect, there is provided a novel N-[2(R)-2,3-epoxypropyl]-3-fluoro-4-(4-morpholinyl)aniline of formula X:

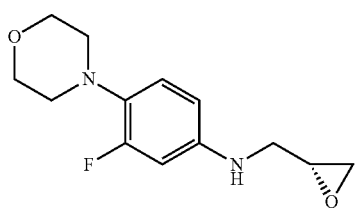

X or an enantiomeric form or a mixture of enantiomeric forms thereof, or a salt thereof.

According to another aspect, there is provided a novel (R)-acetamido-2-hydroxypropyl-carbamate compound of formula XI:

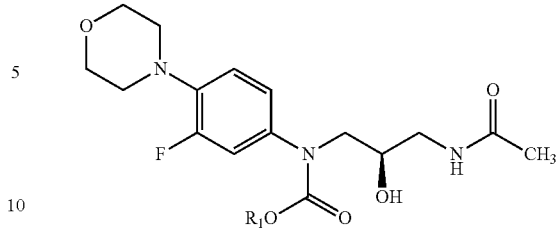

XI or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl.

According to another aspect, there is provided a novel (R)-acetamido-2-acetyloxypropyl-carbamate compound of formula XII:

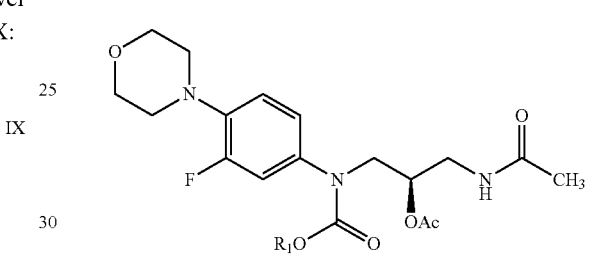

XII or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

In a preferred embodiment, the radical $R_1$ in the compounds of formulae III, IV, V, VI, VII, VIII, IX, XI and XII is methyl, ethyl, propyl, isopropyl, isobutyl, tert-butyl, chloromethyl, phenyl, tolyl, benzyl, p-nitrobenzyl, dibromophenyl or p-methoxybenzyl; and most specifically $R_1$ is methyl, ethyl, benzyl or tert-butyl.

In another embodiment, the leaving group Y in the compound of formulae VII & VIII is a halogen, or an alkyl or aryl sulfonyloxy group. Specifically, the leaving group Y is selected from the group consisting of Cl, Br, I, methanesulfonyloxy, toluenesulfonyloxy and trifluoromethanesulfonyloxy group; more specifically the leaving group Y is Cl or toluenesulfonyloxy; and a most specific leaving group is Cl.

According to another aspect, the present invention also encompasses the use of the novel compounds of formulae III, IV, V, VI, VII, VIII, IX, X, XI and XII disclosed herein for preparing Linezolid.

Instrumental Details:

HPLC Method for Measuring Chemical Purity:

The chemical purity was measured by HPLC using Shimadzu LC-2010 CHT system with LC solutions software or its equivalent under the following conditions: Column=Kromasil 100 C18, 250 mm×4.6 mm, 5 μm or Equivalent; Detector wavelength=254 nm; Flow Rate=0.5 ml/minute; Injection volume=20 μL; Oven temperature=40° C.; Run time=30 minutes; Diluent=Acetonitrile; Elution=Isocratic; Mobile Phase=Water (400 ml):acetonitrile (600 ml):triethyl amine (1.8 ml):acetic acid (1.3 ml).

The following examples are given for the purpose of illustrating the present invention and should not be considered as limitation on the scope or spirit of the invention.

EXAMPLES

Example 1

Preparation of N-[[(5S)-3-[3-fluoro-4-(4-morpholinyl)phenyl]-2-oxo-5-oxazolidinyl]methyl]acetamide (Linezolid)

Step-1: N-[3-Phthalimido-2-(R)-acetyloxypropyl]-N-[3-fluoro-4-(4-morpholinyl)phenyl]-carbamic acid ethyl ester Acetic anhydride (51 g, 0.5 moles) was added to N-[3-phthalimido-2-(R)-hydroxypropyl]-N-[3-fluoro-4-(4-morpholinyl)phenyl]-carbamic acid ethyl ester and the contents were heated to 50-55° C., followed by maintaining the reaction mixture at the same temperature for 4 to 6 hours. After completion of the reaction, the resulting mass was distilled, to remove the excess acetic anhydride, to produce 47.2 g of N-[3-phthalimido-2-(R)-acetyloxypropyl]-N-[3-fluoro-4-(4-morpholinyl)phenyl]-carbamic acid ethyl ester, which is directly used in the next reaction step (Yield: 92%; Purity by HPLC: 98.2%).

Mass (m/z): 514 (M+1).

Step-2: Preparation of Linezolid

Potassium carbonate (12.7 g, 0.092 mol) and hydrazine hydrate (13.8 g, 0.276 mol) were added to a solution of N-[3-phthalimido-2-(R)-acetyloxypropyl]-N-[3-fluoro-4-(4-morpholinyl)phenyl]-carbamic acid ethyl ester (47.2 g, 0.092 mol) in methanol (200 ml) and the mixture was heated to reflux, followed by maintaining the resulting mass at reflux temperature for 4 to 6 hours. After completion of the reaction, the solvent was distilled off completely, water (250 ml) was added to the resulting mass and then extracted with methyl chloride (150 ml×3). The resulting organic layer was washed with water (100 ml×3) and then concentrated to obtain crude product. Ethyl acetate (100 ml) was added to the resulting crude product and then stirred for 1 hour at 25-30° C. The separated solid was filtered and then dried at 70-75° C. to produce 25 g of pure Linezolid as a white crystalline solid (Yield: 81%; Purity by HPLC: 99.8%).

Example 2

Preparation of Linezolid

Potassium carbonate (12.7 g, 0.092 mol) and 40% monomethyl amine (28.5 g, 0.37 mol) were added to a solution of N-[3-phthalimido-2-(R)-acetyloxypropyl]-N-[3-fluoro-4-(4-morpholinyl)phenyl]-carbamic acid ethyl ester (47.2 g, 0.092 mol) in methanol (200 ml) and the mixture was heated to reflux, followed by maintaining the resulting mass at reflux temperature for 4 to 6 hours. After completion of the reaction, the reaction mass was cooled to room temperature (25-30° C.), followed by the addition of water (200 ml) and then stirring the mass for 1 hour at the same temperature. The separated solid was filtered, washed with methanol (50 ml) and then dried at 70-75° C. to produce 26.7 g of pure Linezolid as a white crystalline solid (Yield: 86%; Purity by HPLC: 99.9%).

Example 3

Preparation of (S)—N-[3-Fluoro-4-(4-morpholinyl)phenyl]-2-oxo-5-oxazolidinyl-methylamine Step-1: N-[3-Phthalimido-2-(R)-hydroxypropyl]-N-[3-fluoro-4-(4-morpholinyl)phenyl]-carbamic acid ethyl ester N-Ethyldiisopropyl amine (16 g, 0.124 mol) was added to a suspension of N-[3-phthalimido-2-(R)-hydroxypropyl]-3-fluoro-4-(4-morpholinyl)aniline (39.9 g, 0.1 mol) in methylene chloride (360 ml) at 25-30° C. Ethyl chloroformate (12 g, 0.11 mol) was slowly added to the resulting solution at 25-30° C. during the time period of about 30 minutes, followed by stirring the mass at the same temperature for 1 to 2 hours. The reaction mass was washed subsequently with 4N hydrochloric acid solution (100 ml), water (100 ml) and saturated brine solution (100 ml) and then concentrated the resulting mass to produce 45 g of N-[3-phthalimido-2-(R)-hydroxypropyl]-N-[3-fluoro-4-(4-morpholinyl)phenyl]-carbamic acid ethyl ester as a residue (Yield: 95.5%; Purity by HPLC: 98.5%).

Mass (m/z): 472 (M+1).

Step-2: (S)—N-[3-Fluoro-4-(4-morpholinyl)phenyl]-2-oxo-5-oxazolidinyl-methylamine Potassium carbonate (13.8 g, 0.1 mol) and hydrazine hydrate (80%) (18.75 g, 0.3 mol) were added to a solution of N-[3-phthalimido-2-(R)-hydroxypropyl]-N-[3-fluoro-4-(4-morpholinyl)phenyl]-carbamic acid ethyl ester (47.1 g, 0.1 mol) in methanol (280 ml) and the mixture was heated to reflux, followed by maintaining the resulting mass at reflux for 2 to 4 hours. After completion of the reaction, the solvent was distilled off completely and the resulting crude product was taken in ethylene chloride (200 ml) and the resulting organic layer was washed water (100 ml×3) and then the solvent was distilled off to produce 24.5 g of (S)—N-[3-fluoro-4-(4-morpholinyl)phenyl]-2-oxo-5-oxazolidinyl-methyl amine (Purity by HPLC: 99.1%).

Example 4

Preparation of N-[3-Phthalimido-2-(R)-hydroxypropyl]-N-[3-fluoro-4-(4-morpholinyl)phenyl]-carbamic acid ethyl ester Step-1: N-[3-Chloro-2-(R)-hydroxypropyl]-N-[3-fluoro-4-(4-morpholinyl)phenyl]-carbamic acid ethyl ester N-Ethyldiisopropyl amine (16.1 g, 0.125 mol) was added to a solution of N-[3-chloro-2-(R)-hydroxypropyl]-3-fluoro-4-(4-morpholinyl)aniline (28.85 g, 0.1 mol) in methylene chloride (285 ml) at 25-30° C. Ethyl chloroformate (11 g, 0.1 mol) was added to the resulting solution at 25-30° C., followed by stirring the solution at the same temperature for 4 hours. The reaction mass was washed subsequently with 10% hydrochloric acid solution (100 ml), water (100 ml) and saturated brine solution (100 ml) and then concentrated the resulting mass under reduced pressure to produce 35 g of N-[3-chloro-2-(R)-hydroxypropyl]-N-[3-fluoro-4-(4-morpholinyl)phenyl]-carbamic acid ethyl ester as an oily residue (Yield: 97.2%).

Mass (m/z): 361 (M+1).

Step-2: N-[3-Phthalimido-2-(R)-hydroxypropyl]-N-[3-fluoro-4-(4-morpholinyl)phenyl]-carbamic acid ethyl ester Potassium phthalimide (21.5 g, 0.116 mol) was added to a solution of N-[3-chloro-2-(R)-hydroxypropyl]-N-[3-fluoro-4-(4-morpholinyl)phenyl]-carbamic acid ethyl ester (35 g, 0.097 mol) in dimethylformamide (87.5 ml) and the resulting suspension was heated to 100-110° C. and then maintained for 3 hours at the same temperature. The reaction mass was cooled to room temperature (25-30° C.), followed by the addition of water (400 ml) and then stirring the mass for 1 hour. The separated solid was filtered to produce 30 g of N-[3-phthalimido-2-(R)-hydroxypropyl]-N-[3-fluoro-4-(4-morpholinyl)phenyl]-carbamic acid ethyl ester as an yellow colored solid (Purity by HPLC: 95.8%).

Example 5

Preparation of N-[3-Phthalimido-2-(R)-hydroxypropyl]-N-[3-fluoro-4-(4-morpholinyl)phenyl]-carbamic acid ethyl ester

Step-1: N-[2(R)-2,3-epoxypropyl]-3-fluoro-4-(4-morpholinyl)aniline

50% Sodium hydroxide solution (9 g) and water (30 ml) were added to a solution of N-[3-chloro-2-(R)-hydroxypropyl]-3-fluoro-4-(4-morpholinyl)aniline (28.85 g, 0.1 mol) in methylene chloride (200 ml), followed by stirring the solution for 13 to 14 hours at room temperature (25-30° C.). After completion of the reaction, water (100 ml) was added to the reaction mass, followed by separation of the layers. The solvent was distilled off from the resulting organic layer to get 24.6 g of N-[2(R)-2,3-epoxypropyl]-3-fluoro-4-(4-morpholinyl)aniline as a residue (Yield: 97.6%).

Step-2: N-[2(R)-2,3-epoxypropyl]-N-[3-fluoro-4-(4-morpholinyl)phenyl]-carbamic acid ethyl ester N-Ethyldiisopropyl amine (15.6 g, 0.12 mol) was added to a solution of N-[2(R)-2,3-epoxypropyl]-3-fluoro-4-(4-morpholinyl)aniline (24.6 g, 0.097 mol) in methylene chloride (250 ml) at 25-30° C. Ethyl chloroformate (11 g, 0.1 mol) was added to the resulting solution at 25-30° C., followed by stirring the solution at the same temperature for 2 hours. The reaction mass was washed subsequently with water (100 ml) and saturated brine solution (100 ml×2) and then evaporated the solvent to produce 27.9 g of N-[2(R)-2,3-epoxypropyl]-N-[3-fluoro-4-(4-morpholinyl)phenyl]-carbamic acid ethyl ester (Yield: 88.8%).

Mass (m/z): 325 (M+1).

Step-3: N-[3-Phthalimido-2-(R)-hydroxypropyl]-N-[3-fluoro-4-(4-morpholinyl)phenyl]-carbamic acid ethyl ester Potassium phthalimide (18.5 g, 0.1 mol) was added to a solution of N-[2(R)-2,3-epoxypropyl]-N-[3-fluoro-4-(4-morpholinyl)phenyl]-carbamic acid ethyl ester (27.9 g, 0.086 mol) in dimethylformamide (80 ml) and the resulting suspension was heated to 90-95° C., followed by maintaining the resulting mass for 3 hours at the same temperature. The reaction mass was cooled to room temperature (25-30° C.), followed by the addition of water (400 ml) and then stirring the mass for 1 hour. The separated solid was filtered and then washed with water (50 ml) to produce 28.2 g of N-[3-phthalimido-2-(R)-hydroxypropyl]-N-[3-fluoro-4-(4-morpholinyl)phenyl]-carbamic acid ethyl ester as a cream-yellow colored solid (Purity by HPLC: 95.5%).

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. A process for the preparation of Linezolid of formula I:

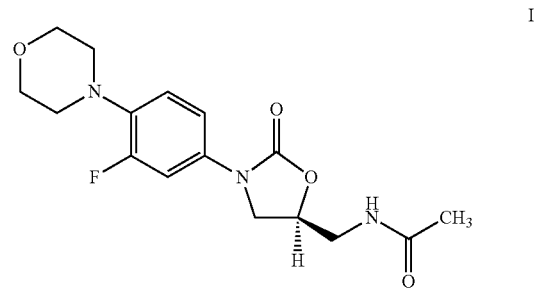 [SMILES: CC(=O)NC[C@H]1CN(c2ccc(N3CCOCC3)c(F)c2)C(=O)O1]

or an enantiomeric form or a mixture of enantiomeric forms thereof, which comprises:

a) acetylating (R)-phthalimido-2-hydroxypropyl-carbamate compound of formula IV:

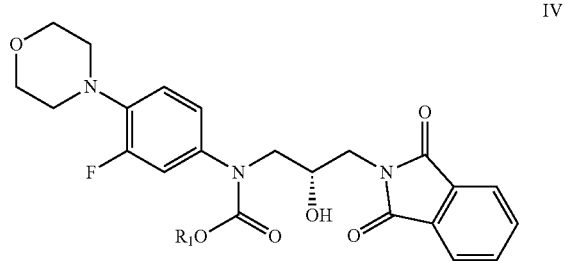

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl;

with an acetylating agent, optionally in the presence of a base, to produce an (R)-phthalimido-2-acetyloxypropyl-carbamate compound of formula III:

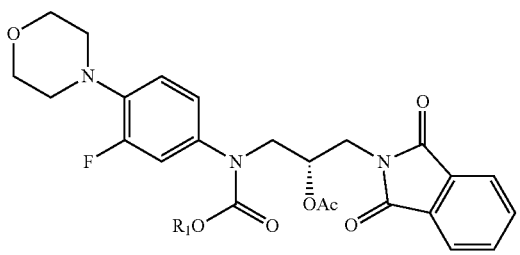

or an enantiomeric form or a mixture of enantiomeric forms thereof, wherein $R_1$ is as defined in formula IV, and 'Ac' represents an acetyl group; and b) reacting the (R)-phthalimido-2-acetyloxypropyl-carbamate compound of formula III with a suitable reagent, optionally in the presence of a base, to produce the Linezolid of formula I.

2. The process of claim 1, wherein the radical $R_1$ in the compounds of formulae III and IV is methyl, ethyl, propyl, isopropyl, isobutyl, tert-butyl, chloromethyl, phenyl, tolyl, benzyl, p-nitrobenzyl, dibromophenyl or p-methoxybenzyl; wherein the acetylating agent used in step-(a) is acetyl chloride, acetyl bromide, acetyl iodide, acetic anhydride, sodium acetate, or a combination thereof; and wherein the reagent used in step-(b) is a primary amine formation agent.

3. The process of claim 2, wherein the radical $R_1$ is methyl, ethyl, benzyl or tert-butyl; wherein the acetylating agent used in step-(a) is acetic anhydride; and wherein the primary amine formation agent used in step-(b) is hydrazine hydrate or aqueous methyl amine.

4. A process for the preparation of Linezolid of formula I:

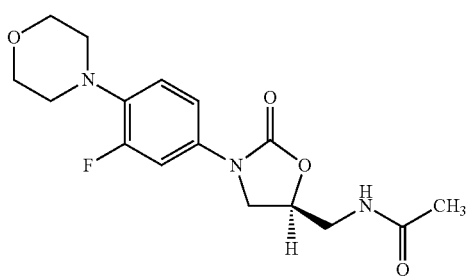

or an enantiomeric form or a mixture of enantiomeric forms thereof, comprising reacting the (R)-phthalimido-2-acetyloxypropyl-carbamate compound of formula III:

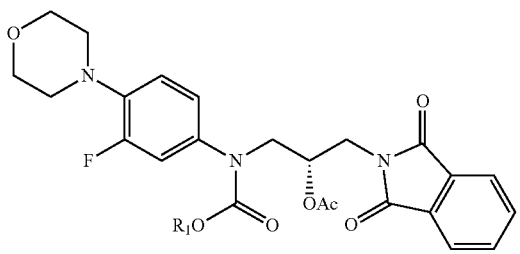

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group;

with a reagent, optionally in the presence of a base, to produce the Linezolid of formula I.

5. The process of claim 4, wherein the radical $R_1$ in the compounds of formula III is methyl, ethyl, propyl, isopropyl, isobutyl, tert-butyl, chloromethyl, phenyl, tolyl, benzyl, p-nitrobenzyl, dibromophenyl or p-methoxybenzyl; and wherein the reagent is hydrazine hydrate or aqueous methyl amine.

6. A process for the preparation of (R)-phthalimido-2-acetyloxypropyl-carbamate compound of formula III:

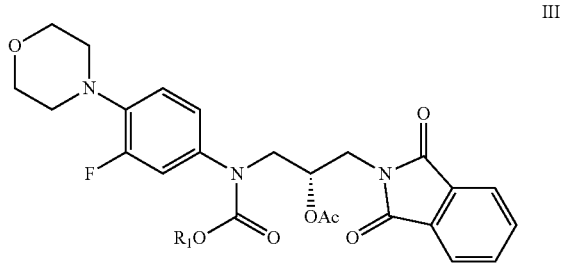

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group;

comprising acetylating (R)-phthalimido-2-hydroxypropyl-carbamate compound of formula IV:

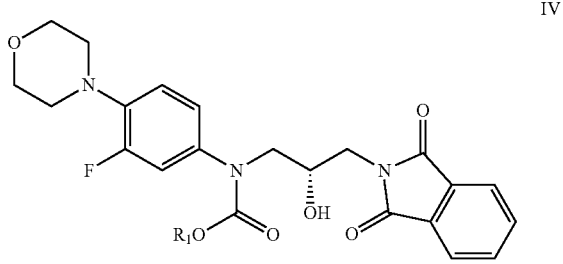

or an enantiomeric form or a mixture of enantiomeric forms thereof, wherein $R_1$ is as defined above; with an acetylating agent optionally in the presence of a base to produce an (R)-phthalimido-2-acetyloxypropyl-carbamate compound of formula III or an enantiomeric form or a mixture of enantiomeric forms thereof.

7. The process of claim 6, wherein the radical $R_1$ in the compounds of formulae III & IV is methyl, ethyl, propyl, isopropyl, isobutyl, tert-butyl, chloromethyl, phenyl, tolyl, benzyl, p-nitrobenzyl, dibromophenyl or p-methoxybenzyl; and wherein the acetylating agent is acetyl chloride, acetyl bromide, acetyl iodide, acetic anhydride, sodium acetate, or a combination thereof.

8. A process for the preparation of Linezolid of formula I:

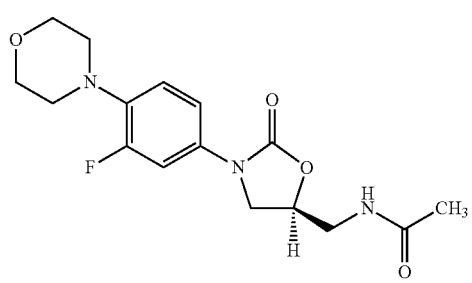

I or an enantiomeric form or a mixture of enantiomeric forms thereof, which comprises:
a) reacting (R)-phthalimido-2-hydroxypropyl-carbamate compound of formula IV:

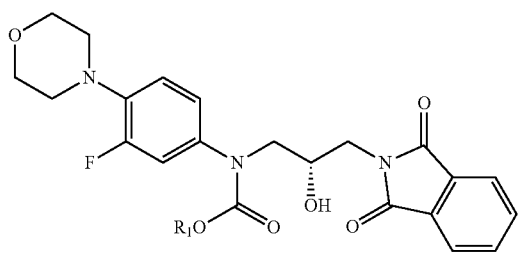

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; with a suitable reagent, optionally in the presence of a base, to produce (S)—N-[3-fluoro-4-(4-morpholinyl)phenyl]-2-oxo-5-oxazolidinyl-methyl amine of formula II:

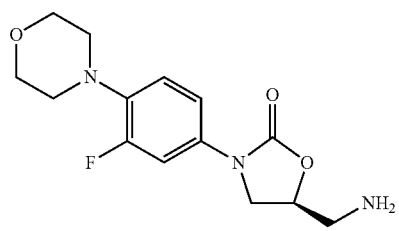

II or an enantiomeric form or a mixture of enantiomeric forms thereof, or a salt thereof; and
b) acetylating the amine compound of formula II with a suitable acetylating agent to produce the Linezolid of formula I.

9. The process of claim 8, wherein the radical $R_1$ in the compounds of formula IV is methyl, ethyl, propyl, isopropyl, isobutyl, tert-butyl, chloromethyl, phenyl, tolyl, benzyl, p-nitrobenzyl, dibromophenyl or p-methoxybenzyl; wherein the reagent used in step-(a) is hydrazine hydrate or aqueous methyl amine; and wherein the acetylating agent used in step-(b) is acetyl chloride, acetyl bromide, acetyl iodide, acetic anhydride, sodium acetate, or a combination thereof.

10. A process for the preparation of (S)—N-[3-fluoro-4-(4-morpholinylphenyl]-2-oxo-5-oxazolidinyl-methyl amine of formula II:

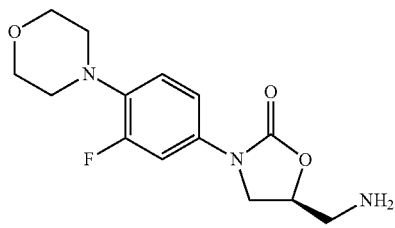

II or an enantiomeric form or a mixture of enantiomeric forms thereof, or a salt thereof;
comprising reacting (R)-phthalimido-2-hydroxypropyl-carbamate compound of formula IV:

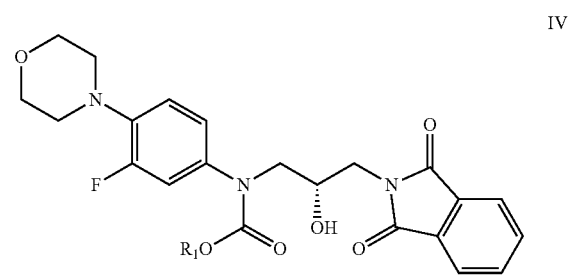

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; with a suitable reagent, optionally in the presence of a base, to produce the aminomethyl compound of formula II, or an enantiomeric form or a mixture of enantiomeric forms thereof, or a salt thereof.

11. The process of claim 10, wherein the radical $R_1$ in the compounds of formulae IV is methyl, ethyl, propyl, isopropyl, isobutyl, tert-butyl, chloromethyl, phenyl, tolyl, benzyl, p-nitrobenzyl, dibromophenyl or p-methoxybenzyl; and wherein the reagent is hydrazine hydrate or aqueous methyl amine.

12. A process for the preparation of (R)-phthalimido-2-hydroxypropyl-carbamate compound of formula IV:

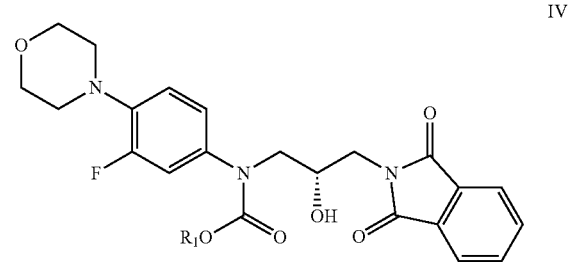

IV or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl;

comprising reacting N-[3-phthalimido-2-(R)-hydroxypropyl]-3-fluoro-4-(4-morpholinyl)aniline of formula XIII:

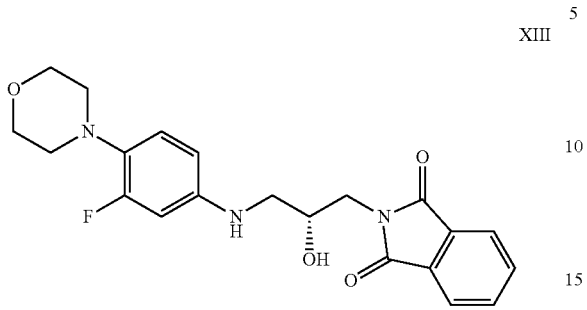

or an enantiomeric form or a mixture of enantiomeric forms thereof, or a salt thereof; with an activating agent, optionally in the presence of a base, wherein the activating agent is a carbonate compound of formula XIVa, or a chloroformate compound of formula XIVb:

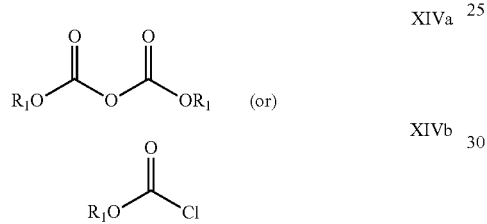

wherein the radical $R_1$ is as defined in Formula IV; to produce the (R)-phthalimido-2-hydroxypropyl-carbamate compound of formula IV or an enantiomeric form or a mixture of enantiomeric forms thereof.

13. The process of claim 12, wherein the radical $R_1$ in the compounds of formulae IV, XIVa & XIVb is methyl, ethyl, propyl, isopropyl, isobutyl, tert-butyl, chloromethyl, phenyl, tolyl, benzyl, p-nitrobenzyl, dibromophenyl or p-methoxybenzyl; wherein the reaction between the compounds of formula XIII and the activating agent is carried out in the presence of a base, wherein the base is an organic or inorganic base; and wherein the reaction is carried out in the presence of a solvent.

14. A process for the preparation of (R)-phthalimido-2-hydroxypropyl-carbamate compound of formula IV:

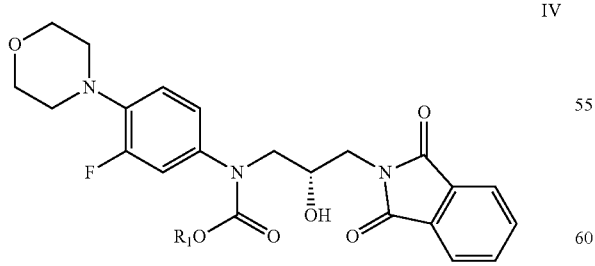

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; which comprises:

a) reacting a (R)-2-hydroxypropyl-aniline compound of formula XV or N-[2(R)-2,3-epoxypropyl]-3-fluoro-4-(4-morpholinyl)aniline of formula X:

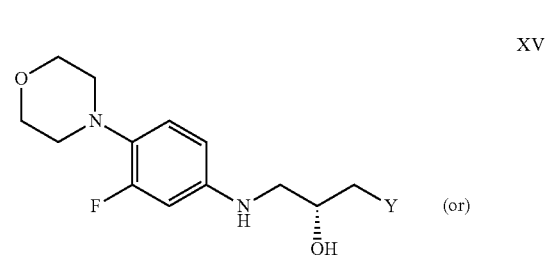

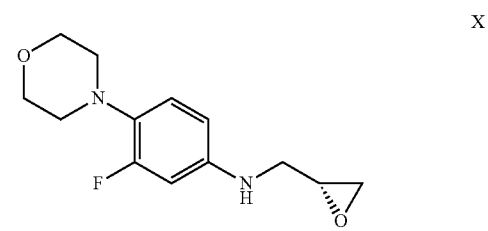

or an enantiomeric form or a mixture of enantiomeric forms thereof, or a salt thereof, wherein Y is a leaving group selected from a halogen or a sulfonyloxy group;

with an activating agent, optionally in the presence of a base, wherein the activating agent is a carbonate compound of formula XIVa, or a chloroformate compound of formula XIVb:

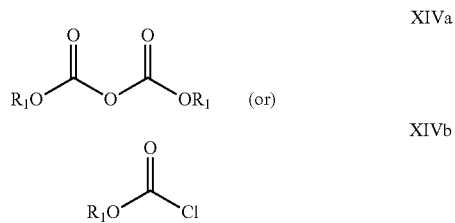

wherein the radical $R_1$ is as defined in Formula IV; to produce an (R)-2-hydroxypropyl-carbamate compound of formula VII or an (R)-2,3-epoxypropyl-carbamate compound of formula IX:

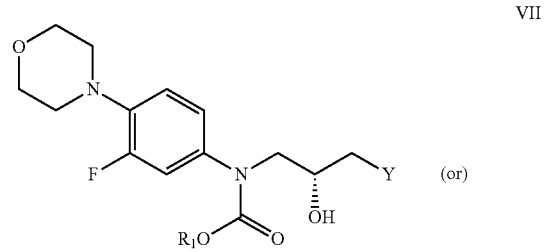

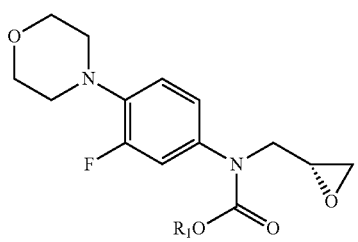

or an enantiomeric form or a mixture of enantiomeric forms thereof, wherein $R_1$ and Y are as defined above; and b) reacting the (R)-2-hydroxypropyl-carbamate compound of formula VII or the (R)-2,3-epoxypropyl-carbamate compound of formula IX obtained in step-(a) with potassium phthalimide, optionally in the presence of a base, to produce the (R)-phthalimido-2-hydroxypropyl-carbamate compound of formula IV or an enantiomeric form or a mixture of enantiomeric forms thereof.

15. The process of claim 14, wherein the radical $R_1$ in the compounds of formulae IV, VII, IX, XIVa & XIVb is methyl, ethyl, propyl, isopropyl, isobutyl, tert-butyl, chloromethyl, phenyl, tolyl, benzyl, p-nitrobenzyl, dibromophenyl or p-methoxybenzyl; and wherein the leaving group Y in the compounds of formulae VII and XV is a halogen, or an alkyl or aryl sulfonyloxy group.

16. A process for the preparation of (R)-phthalimido-2-hydroxypropyl-carbamate compound of formula IV:

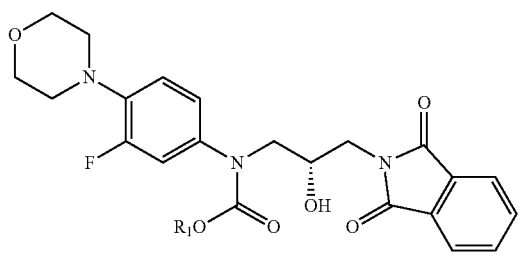

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; comprising reacting the (R)-2-hydroxypropyl-carbamate compound of formula VII or the (R)-2,3-epoxypropyl-carbamate compound of formula IX:

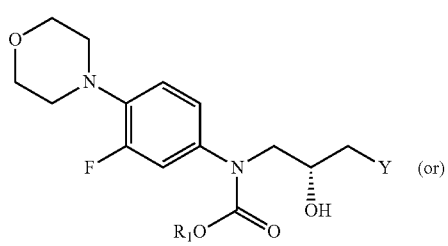

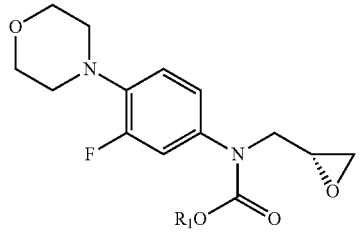

or an enantiomeric form or a mixture of enantiomeric forms thereof, wherein $R_1$ is as defined in Formula IV, and Y is a leaving group selected from a halogen or a sulfonyloxy group; with potassium phthalimide, optionally in the presence of a base, to produce the (R)-phthalimido-2-hydroxypropyl-carbamate compound of formula IV or an enantiomeric form or a mixture of enantiomeric forms thereof.

17. The process of claim 16, wherein the radical $R_1$ in the compounds of formulae IV, VII & IX is methyl, ethyl, propyl, isopropyl, isobutyl, tert-butyl, chloromethyl, phenyl, tolyl, benzyl, p-nitrobenzyl, dibromophenyl or p-methoxybenzyl; and wherein the leaving group Y is selected from the group consisting of Cl, Br, I, methanesulfonyloxy, toluenesulfonyloxy and trifluoromethanesulfonyloxy group.

18. A process for the preparation of (R)-phthalimido-2-hydroxypropyl-carbamate compound of formula IV:

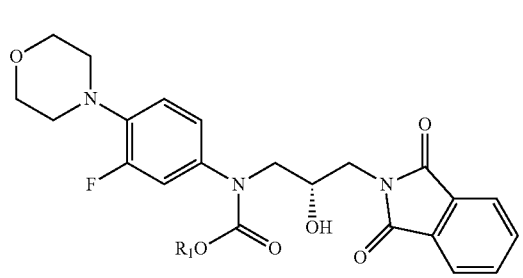

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; which comprises:

a) reacting a (R)-2-hydroxypropyl-aniline compound of formula XV or N-[2(R)-2,3-epoxypropyl]-3-fluoro-4-(4-morpholinyl)aniline of formula X:

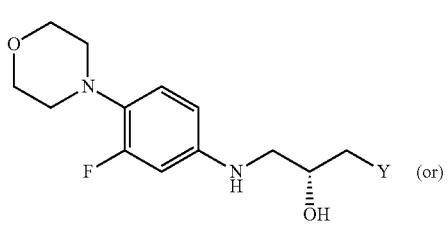

-continued

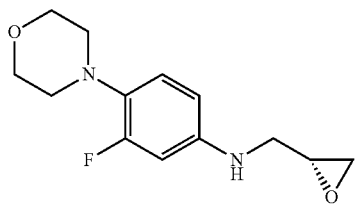

X or an enantiomeric form or a mixture of enantiomeric forms thereof, or a salt thereof, wherein Y is a leaving group selected from a halogen or a sulfonyloxy group; with potassium phthalimide, optionally in the presence of a base, to produce N-[3-phthalimido-2-(R)-hydroxypropyl]-3-fluoro-4-(4-morpholinyl)aniline of formula XIII:

XIII

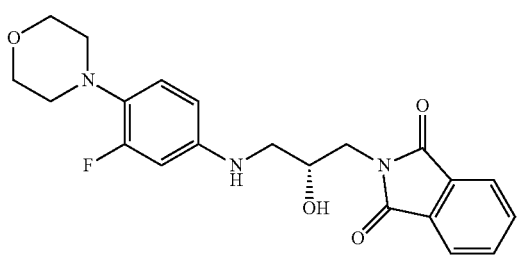

or an enantiomeric form or a mixture of enantiomeric forms thereof, or a salt thereof; and b) reacting the N-[3-phthalimido-2-(R)-hydroxypropyl]-3-fluoro-4-(4-morpholinyl)aniline of formula XIII or an enantiomeric form or a mixture of enantiomeric forms thereof, or a salt thereof; with an activating agent, optionally in the presence of a base, wherein the activating agent is a carbonate compound of formula XIVa, or a chloroformate compound of formula XIVb:

XIVa

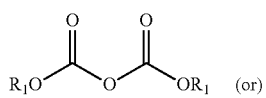  (or)

XIVb

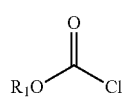

wherein the radical $R_1$ is as defined in Formula IV; to produce the (R)-phthalimido-2-hydroxypropyl-carbamate compound of formula IV or an enantiomeric form or a mixture of enantiomeric forms thereof.

19. The process of claim 18, wherein the radical $R_1$ in the compounds of formulae IV, XIVa & XIVb is methyl, ethyl, propyl, isopropyl, isobutyl, tert-butyl, chloromethyl, phenyl, tolyl, benzyl, p-nitrobenzyl, dibromophenyl or p-methoxybenzyl; and wherein the leaving group Y in the compound of formula XV is selected from the group consisting of Cl, Br, I, methanesulfonyloxy, toluenesulfonyloxy and trifluoromethanesulfonyloxy group.

20. A (R)-phthalimido-2-acetyloxypropyl-carbamate compound of formula III:

III

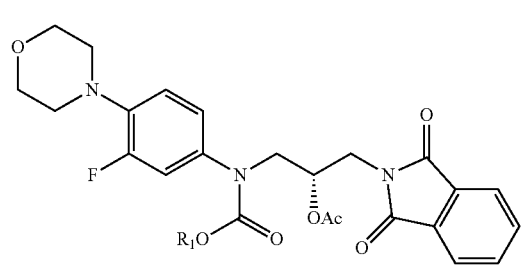

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

21. The compound of claim 20, wherein the radical $R_1$ is methyl, ethyl, propyl, isopropyl, isobutyl, tert-butyl, chloromethyl, phenyl, tolyl, benzyl, p-nitrobenzyl, dibromophenyl or p-methoxybenzyl.

22. A (R)-amino-2-acetyloxypropyl-carbamate compound of formula V:

V

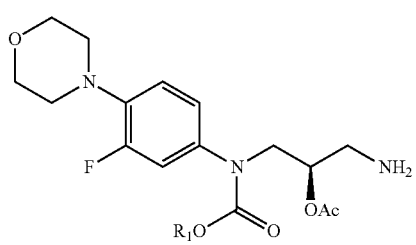

or an enantiomeric form or a mixture of enantiomeric forms thereof, wherein $R_1$ is $C_{1-12}$ straight or branched chain alkyl, cycloalkyl, haloalkyl, substituted or unsubstituted aryl, or substituted or unsubstituted aralkyl; and 'Ac' represents an acetyl group.

23. The compound of claim 22, wherein the radical $R_1$ is methyl, ethyl, propyl, isopropyl, isobutyl, tert-butyl, chloromethyl, phenyl, tolyl, benzyl, p-nitrobenzyl, dibromophenyl or p-methoxybenzyl.

* * * * *